United States Patent
Jackels et al.

(10) Patent No.: US 9,668,926 B2
(45) Date of Patent: Jun. 6, 2017

(54) METHOD AND APPARATUS FOR MAKING ABSORBENT STRUCTURES WITH ABSORBENT MATERIAL

(75) Inventors: Hans Adolf Jackels, Euskircken (DE); Carsten Heinrich Kreuzer, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/491,902

(22) Filed: Jun. 8, 2012

(65) Prior Publication Data

US 2012/0316046 A1   Dec. 13, 2012

(30) Foreign Application Priority Data

Jun. 10, 2011 (EP) .................................... 11169395

(51) Int. Cl.
| | |
|---|---|
| *B05D 5/10* | (2006.01) |
| *B31B 49/00* | (2006.01) |
| *A61F 13/53* | (2006.01) |
| *A61F 13/514* | (2006.01) |
| *A61F 13/532* | (2006.01) |
| *A61F 13/539* | (2006.01) |

(52) U.S. Cl.
CPC ............ *A61F 13/53* (2013.01); *A61F 13/514* (2013.01); *A61F 13/5323* (2013.01); *A61F 2013/53908* (2013.01)

(58) Field of Classification Search
CPC ...... A61F 13/16; A61F 3/15699; A61F 13/53; A61F 13/514; A61F 13/5323; A61F 2013/53908

USPC ......... 156/199, 201, 276; 604/382; 493/331, 493/374

See application file for complete search history.

(56) References Cited

U.S. PATENT DOCUMENTS

| | | | |
|---|---|---|---|
| 1,733,997 | A | 10/1929 | Marr |
| 1,734,499 | A | 11/1929 | Marinsky |
| 1,989,283 | A | 1/1935 | Limacher |
| 2,058,509 | A | 10/1936 | Rose |
| 2,271,676 | A | 2/1942 | Bjornbak |
| 2,450,789 | A | 10/1948 | Frieman |
| 2,508,811 | A | 5/1950 | Best et al. |
| 2,568,910 | A | 9/1951 | Condylis |
| 2,570,796 | A | 10/1951 | Gross |
| 2,570,963 | A | 10/1951 | Mesmer |

(Continued)

FOREIGN PATENT DOCUMENTS

| | | |
|---|---|---|
| CA | 2001370 | 4/1990 |
| CA | 2291997 | 6/2000 |

(Continued)

OTHER PUBLICATIONS

PCT International Search Report dated Oct. 11, 2012, 12 pages.

*Primary Examiner* — Matthew Daniels
*Assistant Examiner* — Marta Dulko
(74) *Attorney, Agent, or Firm* — Charles R. Matson

(57) ABSTRACT

A method and apparatus for making specific absorbent structures with an absorbent layer with absorbent material with therein substantially longitudinally extending strips that are free of absorbent material, using or having thereto a moving endless surface with receptacle(s) with specific longitudinally extending rods; and specific absorbent structures obtained therewith, suitable for absorbent articles, such as diapers and sanitary napkins.

5 Claims, 5 Drawing Sheets

(56) References Cited

U.S. PATENT DOCUMENTS

| | | |
|---|---|---|
| 2,583,553 A | 1/1952 | Faure |
| 2,705,957 A | 4/1955 | Mauro |
| 2,788,003 A | 4/1957 | Norden |
| 2,788,786 A | 4/1957 | Dexter |
| 2,798,489 A | 7/1957 | Behrman |
| 2,807,263 A | 9/1957 | Newton |
| 2,830,589 A | 4/1958 | Doner |
| 2,890,700 A | 6/1959 | Lönberg-Holm |
| 2,890,701 A | 6/1959 | Weinman |
| 2,898,912 A | 8/1959 | Adams |
| 2,931,361 A | 4/1960 | Sostsrin |
| 2,977,957 A | 4/1961 | Clyne |
| 3,071,138 A | 1/1963 | Gustavo |
| 3,180,335 A | 4/1965 | Duncan et al. |
| 3,207,158 A | 9/1965 | Yoshitake et al. |
| 3,386,442 A | 6/1968 | Sabee |
| 3,561,446 A | 2/1971 | Jones |
| 3,572,342 A | 3/1971 | Lindquist et al. |
| 3,572,432 A | 3/1971 | Burton |
| 3,575,174 A | 4/1971 | Mogor |
| 3,578,155 A | 5/1971 | Small et al. |
| 3,606,887 A | 9/1971 | Roeder |
| 3,610,244 A | 10/1971 | Jones |
| 3,618,608 A | 11/1971 | Brink |
| 3,642,001 A | 2/1972 | Sabee |
| 3,653,381 A | 4/1972 | Warnken |
| 3,670,731 A | 6/1972 | Harmon |
| 3,688,767 A | 9/1972 | Goldstein |
| 3,710,797 A | 1/1973 | Marsan |
| 3,731,688 A | 5/1973 | Litt et al. |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand et al. |
| 3,840,418 A | 10/1974 | Sabee |
| 3,847,702 A | 11/1974 | Jones |
| 3,848,594 A | 11/1974 | Buell |
| 3,848,595 A | 11/1974 | Endres |
| 3,848,597 A | 11/1974 | Endres |
| 3,860,003 A | 1/1975 | Buell |
| 3,863,637 A | 2/1975 | MacDonald et al. |
| 3,882,870 A | 5/1975 | Hathaway |
| 3,884,234 A | 5/1975 | Taylor |
| 3,900,032 A | 8/1975 | Heurlen |
| 3,911,173 A | 10/1975 | Sprague, Jr. |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,055,180 A | 10/1977 | Karami |
| 4,059,114 A | 11/1977 | Richards |
| 4,074,508 A | 2/1978 | Reid |
| 4,084,592 A | 4/1978 | Tritsch |
| 4,100,922 A | 7/1978 | Hernandez |
| 4,154,883 A | 5/1979 | Elias |
| 4,232,674 A | 11/1980 | Melican |
| 4,257,418 A | 3/1981 | Hessner |
| 4,259,220 A | 3/1981 | Bunnelle et al. |
| 4,296,750 A | 10/1981 | Woon et al. |
| 4,315,508 A | 2/1982 | Bolick |
| 4,324,246 A | 4/1982 | Mullane et al. |
| 4,340,706 A | 7/1982 | Obayashi et al. |
| 4,341,216 A | 7/1982 | Obenour |
| 4,342,314 A | 8/1982 | Radel et al. |
| 4,381,783 A | 5/1983 | Elias |
| 4,388,075 A | 6/1983 | Mesek et al. |
| 4,461,621 A | 7/1984 | Karami et al. |
| 4,463,045 A | 7/1984 | Ahr et al. |
| 4,469,710 A | 9/1984 | Rielley et al. |
| 4,475,912 A | 10/1984 | Coates |
| 4,490,148 A | 12/1984 | Beckeström |
| 4,507,438 A | 3/1985 | Obayashi et al. |
| 4,515,595 A | 5/1985 | Kievet et al. |
| 4,527,990 A | 7/1985 | Sigl |
| 4,541,871 A | 9/1985 | Obayashi et al. |
| 4,573,986 A | 3/1986 | Minetola et al. |
| 4,578,072 A | 3/1986 | Lancaster |
| 4,585,448 A | 4/1986 | Enloe |
| 4,585,450 A | 4/1986 | Rosch et al. |
| 4,589,878 A | 5/1986 | Mitrani |
| 4,596,568 A | 6/1986 | Flug |
| 4,601,717 A | 7/1986 | Blevins |
| 4,606,964 A | 8/1986 | Wideman |
| 4,609,518 A | 9/1986 | Curro et al. |
| 4,610,678 A | 9/1986 | Weisman et al. |
| 4,623,342 A | 11/1986 | Ito et al. |
| 4,624,666 A | 11/1986 | Derossett |
| 4,629,643 A | 12/1986 | Curro et al. |
| 4,636,207 A | 1/1987 | Buell |
| 4,641,381 A | 2/1987 | Heran et al. |
| 4,662,875 A | 5/1987 | Hirotsu et al. |
| 4,666,983 A | 5/1987 | Tsubakimoto et al. |
| 4,670,011 A | 6/1987 | Mesek |
| 4,670,012 A | 6/1987 | Johnson |
| 4,680,030 A | 7/1987 | Coates et al. |
| 4,681,579 A | 7/1987 | Toussant et al. |
| 4,681,581 A | 7/1987 | Coates |
| 4,681,793 A | 7/1987 | Linman et al. |
| 4,690,680 A | 9/1987 | Higgins |
| 4,695,278 A | 9/1987 | Lawson |
| 4,699,622 A | 10/1987 | Toussant et al. |
| 4,704,115 A | 11/1987 | Buell |
| 4,704,116 A | 11/1987 | Enloe |
| 4,710,189 A | 12/1987 | Lash |
| 4,731,066 A | 3/1988 | Korpman |
| 4,731,070 A | 3/1988 | Koci |
| RE32,649 E | 4/1988 | Brandt et al. |
| 4,747,846 A | 5/1988 | Boland et al. |
| 4,773,905 A | 9/1988 | Molee |
| 4,784,892 A | 11/1988 | Storey et al. |
| 4,785,996 A | 11/1988 | Ziecker et al. |
| 4,787,896 A | 11/1988 | Houghton et al. |
| 4,795,454 A | 1/1989 | Dragoo |
| 4,802,884 A | 2/1989 | Fröidh et al. |
| 4,808,176 A | 2/1989 | Kielpikowski |
| 4,808,178 A | 2/1989 | Aziz |
| 4,834,735 A | 5/1989 | Alemany et al. |
| 4,834,740 A | 5/1989 | Suzuki et al. |
| 4,834,742 A | 5/1989 | Wilson et al. |
| 4,838,886 A | 6/1989 | Kent |
| 4,842,666 A | 6/1989 | Werenicz |
| 4,846,815 A | 7/1989 | Scripps |
| 4,846,825 A | 7/1989 | Enloe et al. |
| 4,861,652 A | 8/1989 | Lippert et al. |
| 4,869,724 A | 9/1989 | Scripps |
| 4,886,697 A | 12/1989 | Perdelwitz, Jr et al. |
| 4,888,231 A | 12/1989 | Angstadt |
| 4,892,528 A | 1/1990 | Suzuki et al. |
| 4,892,535 A | 1/1990 | Bjornberg |
| 4,892,536 A | 1/1990 | DesMarais et al. |
| 4,894,060 A | 1/1990 | Nestegard |
| 4,894,277 A | 1/1990 | Akasaki |
| 4,900,317 A | 2/1990 | Buell |
| 4,904,251 A | 2/1990 | Igaue et al. |
| 4,909,802 A | 3/1990 | Ahr et al. |
| 4,909,803 A | 3/1990 | Aziz et al. |
| 4,936,839 A | 6/1990 | Molee |
| 4,940,463 A | 7/1990 | Leathers et al. |
| 4,940,464 A | 7/1990 | Van Gompel et al. |
| 4,946,527 A | 8/1990 | Battrell |
| 4,950,264 A | 8/1990 | Osborn |
| 4,960,477 A | 10/1990 | Mesek |

(56) References Cited

U.S. PATENT DOCUMENTS

| | | |
|---|---|---|
| 4,963,140 A | 10/1990 | Robertson et al. |
| 4,968,313 A | 11/1990 | Sabee |
| 4,990,147 A | 2/1991 | Freeland |
| 4,994,053 A | 2/1991 | Lang |
| 5,006,394 A | 4/1991 | Baird |
| 5,019,063 A | 5/1991 | Marsan et al. |
| 5,019,072 A | 5/1991 | Polski |
| 5,021,051 A | 6/1991 | Hiuke |
| 5,030,314 A | 7/1991 | Lang |
| 5,032,120 A | 7/1991 | Freeland et al. |
| 5,034,008 A | 7/1991 | Breitkopf |
| 5,037,416 A | 8/1991 | Allen et al. |
| 5,071,414 A | 12/1991 | Elliott |
| 5,072,687 A | 12/1991 | Mitchell |
| 5,076,774 A | 12/1991 | Farrington et al. |
| 5,085,654 A | 2/1992 | Buell |
| 5,087,255 A | 2/1992 | Sims et al. |
| 5,092,861 A | 3/1992 | Nomura et al. |
| 5,102,597 A | 4/1992 | Roe et al. |
| 5,114,420 A | 5/1992 | Igaue et al. |
| 5,124,188 A | 6/1992 | Roe et al. |
| 5,135,522 A | 8/1992 | Fahrenkrug et al. |
| 5,137,537 A | 8/1992 | Herron et al. |
| D329,697 S | 9/1992 | Fahrenkrug et al. |
| 5,143,679 A | 9/1992 | Weber et al. |
| 5,147,343 A | 9/1992 | Kellenberger |
| 5,147,345 A | 9/1992 | Young et al. |
| 5,149,334 A | 9/1992 | Roe et al. |
| 5,149,335 A | 9/1992 | Kellenberger et al. |
| 5,151,091 A | 9/1992 | Glaug |
| 5,151,092 A | 9/1992 | Buell et al. |
| 5,156,793 A | 10/1992 | Buell et al. |
| 5,167,653 A | 12/1992 | Igaue et al. |
| 5,167,897 A | 12/1992 | Weber et al. |
| 5,175,046 A | 12/1992 | Nguyen |
| 5,180,622 A | 1/1993 | Berg et al. |
| 5,190,563 A | 3/1993 | Herron et al. |
| 5,190,606 A | 3/1993 | Merkatoris et al. |
| 5,204,997 A | 4/1993 | Suzuki et al. |
| 5,221,274 A | 6/1993 | Buell et al. |
| 5,235,515 A | 8/1993 | Ungpiyakul et al. |
| 5,242,436 A | 9/1993 | Weil et al. |
| 5,246,431 A | 9/1993 | Minetola et al. |
| 5,246,432 A | 9/1993 | Suzuki et al. |
| 5,246,433 A | 9/1993 | Hasse et al. |
| 5,248,309 A | 9/1993 | Serbiak et al. |
| 5,260,345 A | 11/1993 | Desmarais et al. |
| 5,269,775 A | 12/1993 | Freeland et al. |
| 5,281,683 A | 1/1994 | Yano et al. |
| H1298 H | 4/1994 | Ahr |
| 5,300,565 A | 4/1994 | Berg et al. |
| 5,312,386 A | 5/1994 | Correa et al. |
| 5,331,059 A | 7/1994 | Engelhardt et al. |
| 5,336,552 A | 8/1994 | Strack et al. |
| 5,348,547 A | 9/1994 | Payne et al. |
| 5,358,500 A | 10/1994 | LaVon et al. |
| 5,366,782 A | 11/1994 | Curro et al. |
| 5,387,207 A | 2/1995 | Dyer et al. |
| 5,387,209 A | 2/1995 | Yamamoto et al. |
| 5,389,095 A | 2/1995 | Suzuki |
| 5,397,316 A | 3/1995 | Lavon et al. |
| 5,399,175 A | 3/1995 | Glaug |
| 5,401,792 A | 3/1995 | Babu et al. |
| 5,409,771 A | 4/1995 | Dahmen et al. |
| H1440 H | 5/1995 | New et al. |
| 5,411,497 A | 5/1995 | Tanzer et al. |
| 5,415,644 A | 5/1995 | Enloe |
| 5,425,725 A | 6/1995 | Tanzer et al. |
| 5,433,715 A | 7/1995 | Tanzer et al. |
| 5,451,219 A | 9/1995 | Suzuki |
| 5,451,442 A | 9/1995 | Pieniak |
| 5,460,622 A | 10/1995 | Dragoo et al. |
| 5,462,541 A | 10/1995 | Bruemmer et al. |
| 5,466,409 A | 11/1995 | Partridge et al. |
| 5,476,458 A | 12/1995 | Glaug et al. |
| 5,486,166 A | 1/1996 | Bishop et al. |
| 5,490,846 A | 2/1996 | Ellis et al. |
| 5,492,962 A | 2/1996 | Lahrman et al. |
| 5,494,622 A | 2/1996 | Heath et al. |
| 5,499,978 A | 3/1996 | Buell et al. |
| 5,507,736 A | 4/1996 | Clear et al. |
| 5,507,895 A | 4/1996 | Suekane |
| 5,509,915 A | 4/1996 | Hanson et al. |
| 5,514,104 A | 5/1996 | Cole |
| 5,518,801 A | 5/1996 | Chappell et al. |
| 5,520,674 A | 5/1996 | Hines et al. |
| 5,522,810 A | 6/1996 | Allen, Jr. |
| 5,527,300 A | 6/1996 | Sauer |
| 5,531,730 A | 7/1996 | Dreier |
| 5,532,323 A | 7/1996 | Yano et al. |
| 5,536,341 A | 7/1996 | Kelman |
| 5,542,943 A | 8/1996 | Sageser |
| 5,549,592 A | 8/1996 | Fries et al. |
| 5,549,593 A | 8/1996 | Ygge et al. |
| 5,549,791 A | 8/1996 | Herron et al. |
| 5,554,145 A | 9/1996 | Roe et al. |
| 5,560,878 A | 10/1996 | Dragoo et al. |
| 5,562,646 A | 10/1996 | Goldman et al. |
| 5,569,234 A | 10/1996 | Buell et al. |
| 5,571,096 A | 11/1996 | Dobrin et al. |
| 5,574,121 A | 11/1996 | Irie et al. |
| 5,580,411 A | 12/1996 | Nease et al. |
| 5,584,829 A | 12/1996 | Lavash et al. |
| 5,591,152 A | 1/1997 | Buell et al. |
| 5,591,155 A | 1/1997 | Nishikawa et al. |
| 5,593,399 A | 1/1997 | Tanzer et al. |
| 5,599,335 A | 2/1997 | Goldman et al. |
| 5,601,542 A | 2/1997 | Melius et al. |
| 5,607,414 A | 3/1997 | Richards et al. |
| 5,607,416 A | 3/1997 | Yamamoto et al. |
| 5,607,537 A | 3/1997 | Johnson et al. |
| 5,607,760 A | 3/1997 | Roe et al. |
| 5,609,587 A | 3/1997 | Roe |
| 5,609,588 A | 3/1997 | DiPalma et al. |
| 5,611,879 A | 3/1997 | Morman |
| 5,613,959 A | 3/1997 | Roessler et al. |
| 5,613,960 A | 3/1997 | Mizutani |
| 5,614,283 A | 3/1997 | Potnis et al. |
| 5,622,589 A | 4/1997 | Johnson et al. |
| 5,624,423 A | 4/1997 | Anjur |
| 5,624,424 A | 4/1997 | Saisaka et al. |
| 5,626,571 A | 5/1997 | Young et al. |
| 5,628,741 A | 5/1997 | Buell et al. |
| 5,635,191 A | 6/1997 | Roe et al. |
| 5,635,271 A | 6/1997 | Zafiroglu |
| 5,637,106 A | 6/1997 | Mitchell |
| 5,643,238 A | 7/1997 | Baker |
| 5,643,243 A | 7/1997 | Klemp |
| 5,643,588 A | 7/1997 | Roe et al. |
| 5,649,914 A | 7/1997 | Glaug |
| 5,650,214 A | 7/1997 | Anderson |
| H1674 H | 8/1997 | Ames et al. |
| 5,658,268 A | 8/1997 | Johns et al. |
| 5,662,634 A | 9/1997 | Yamamoto et al. |
| 5,662,638 A | 9/1997 | Johnson et al. |
| 5,665,396 A | 9/1997 | Ulman |
| 5,674,215 A | 10/1997 | Ronnberg |
| 5,683,374 A | 11/1997 | Yamamoto |
| 5,685,874 A | 11/1997 | Buell et al. |
| 5,690,627 A | 11/1997 | Clear et al. |
| 5,691,035 A | 11/1997 | Chappell et al. |
| 5,691,036 A | 11/1997 | Lin et al. |
| 5,695,488 A | 12/1997 | Sosalla |
| 5,700,254 A | 12/1997 | McDowall et al. |
| 5,702,376 A | 12/1997 | Glaug |
| 5,714,156 A | 2/1998 | Schmidt et al. |
| 5,723,087 A | 3/1998 | Chappell et al. |
| 5,733,275 A | 3/1998 | Davis et al. |
| 5,749,866 A | 5/1998 | Roe et al. |
| 5,752,947 A | 5/1998 | Awolin |
| 5,756,039 A | 5/1998 | Mcfall et al. |
| H1732 H | 6/1998 | Johnson |
| 5,762,641 A | 6/1998 | Bewick Sonntag et al. |
| 5,766,388 A | 6/1998 | Pelley |

(56) References Cited

U.S. PATENT DOCUMENTS

| | | |
|---|---|---|
| 5,766,389 A | 6/1998 | Brandon et al. |
| 5,772,825 A | 6/1998 | Schmitz |
| 5,776,121 A | 7/1998 | Roe et al. |
| 5,779,831 A | 7/1998 | Schmitz |
| 5,788,684 A | 8/1998 | Abuto et al. |
| 5,795,345 A | 8/1998 | Mizutani |
| 5,797,892 A | 8/1998 | Glaug |
| 5,797,894 A | 8/1998 | Cadieux et al. |
| 5,807,365 A | 9/1998 | Luceri |
| 5,810,796 A | 9/1998 | Kimura et al. |
| 5,810,800 A | 9/1998 | Hunter et al. |
| 5,814,035 A | 9/1998 | Gryskiewicz et al. |
| 5,820,618 A | 10/1998 | Roberts et al. |
| 5,827,257 A | 10/1998 | Fujioka |
| 5,830,202 A | 11/1998 | Bogdanski et al. |
| 5,833,678 A | 11/1998 | Ashton et al. |
| 5,837,789 A | 11/1998 | Stockhausen et al. |
| 5,843,059 A | 12/1998 | Niemeyer et al. |
| 5,846,231 A | 12/1998 | Fujioka et al. |
| 5,846,232 A | 12/1998 | Serbiak et al. |
| 5,849,816 A | 12/1998 | Suskind et al. |
| 5,851,204 A | 12/1998 | Mizutani |
| 5,855,572 A | 1/1999 | Schmidt |
| 5,858,013 A | 1/1999 | Kling |
| 5,865,823 A | 2/1999 | Curro |
| 5,865,824 A | 2/1999 | Chen |
| 5,873,868 A | 2/1999 | Nakahata |
| 5,876,391 A | 3/1999 | Roe et al. |
| 5,891,118 A | 4/1999 | Toyoshima |
| 5,891,544 A | 4/1999 | Chappell et al. |
| 5,897,545 A | 4/1999 | Kline et al. |
| 5,904,673 A | 5/1999 | Roe et al. |
| 5,928,184 A | 7/1999 | Etheredge |
| 5,931,825 A | 8/1999 | Kuen et al. |
| 5,938,648 A | 8/1999 | Lavon et al. |
| 5,938,650 A | 8/1999 | Baer et al. |
| 5,941,862 A | 8/1999 | Haynes et al. |
| 5,944,706 A | 8/1999 | Palumbo et al. |
| 5,947,949 A | 9/1999 | Inoue et al. |
| 5,951,536 A | 9/1999 | Osborn, III et al. |
| 5,957,908 A | 9/1999 | Kline et al. |
| 5,968,025 A | 10/1999 | Roe et al. |
| 5,968,029 A | 10/1999 | Chappell et al. |
| 5,980,500 A | 11/1999 | Shimizu et al. |
| 5,981,824 A | 11/1999 | Luceri |
| 5,989,236 A | 11/1999 | Roe et al. |
| 6,004,306 A | 12/1999 | Robles et al. |
| 6,022,430 A | 2/2000 | Blenke et al. |
| 6,022,431 A | 2/2000 | Blenke et al. |
| 6,042,673 A | 3/2000 | Johnson et al. |
| 6,050,984 A | 4/2000 | Fujioka |
| 6,054,631 A | 4/2000 | Gent |
| 6,060,115 A | 5/2000 | Borowski et al. |
| 6,068,620 A | 5/2000 | Chmielewski |
| 6,080,909 A | 6/2000 | Osterdahl et al. |
| 6,083,210 A | 7/2000 | Young et al. |
| 6,090,994 A | 7/2000 | Chen |
| 6,091,336 A | 7/2000 | Zand |
| 6,099,515 A | 8/2000 | Sugito |
| 6,102,892 A | 8/2000 | Putzer et al. |
| 6,103,814 A | 8/2000 | Van Drongelen et al. |
| 6,107,537 A | 8/2000 | Elder et al. |
| 6,110,157 A | 8/2000 | Schmidt |
| 6,117,121 A | 9/2000 | Faulks et al. |
| 6,117,803 A | 9/2000 | Morman et al. |
| 6,120,486 A | 9/2000 | Toyoda et al. |
| 6,120,487 A | 9/2000 | Ashton |
| 6,120,489 A | 9/2000 | Johnson et al. |
| 6,120,866 A | 9/2000 | Arakawa et al. |
| 6,121,509 A | 9/2000 | Ashraf et al. |
| 6,129,717 A | 10/2000 | Fujioka et al. |
| 6,129,720 A | 10/2000 | Blenke et al. |
| 6,132,411 A | 10/2000 | Huber et al. |
| 6,139,912 A | 10/2000 | Onuschak |
| 6,143,821 A | 11/2000 | Houben |
| 6,152,908 A | 11/2000 | Widlund |
| 6,156,023 A | 12/2000 | Yoshioka |
| 6,156,424 A | 12/2000 | Taylor |
| 6,160,197 A | 12/2000 | Lassen |
| 6,165,160 A | 12/2000 | Suzuki et al. |
| 6,174,302 B1 | 1/2001 | Kumasaka |
| 6,177,606 B1 | 1/2001 | Etheredge |
| 6,177,607 B1 | 1/2001 | Blaney et al. |
| 6,186,996 B1 | 2/2001 | Martin |
| 6,210,386 B1 | 4/2001 | Inoue |
| 6,210,390 B1 | 4/2001 | Karlsson |
| 6,231,556 B1 | 5/2001 | Osborn, III |
| 6,231,566 B1 | 5/2001 | Lai |
| 6,238,380 B1 | 5/2001 | Sasaki |
| 6,241,716 B1 | 6/2001 | Rönnberg |
| 6,258,996 B1 | 7/2001 | Goldman |
| 6,265,488 B1 | 7/2001 | Fujino et al. |
| 6,306,122 B1 | 10/2001 | Narawa et al. |
| 6,315,765 B1 | 11/2001 | Datta |
| 6,322,552 B1 | 11/2001 | Blenke et al. |
| 6,325,787 B1 | 12/2001 | Roe et al. |
| 6,326,525 B1 | 12/2001 | Hamajima |
| 6,330,735 B1 | 12/2001 | Hahn et al. |
| 6,334,858 B1 | 1/2002 | Rönnberg et al. |
| 6,336,922 B1 | 1/2002 | Van Gompel et al. |
| 6,340,611 B1 | 1/2002 | Shimizu |
| 6,342,715 B1 | 1/2002 | Shimizu |
| 6,350,332 B1 | 2/2002 | Thomas et al. |
| 6,368,687 B1 | 4/2002 | Joseph et al. |
| 6,371,948 B1 | 4/2002 | Mizutani |
| 6,372,952 B1 | 4/2002 | Lash et al. |
| 6,375,644 B2 | 4/2002 | Mizutani |
| 6,376,034 B1 | 4/2002 | Brander |
| 6,383,431 B1 | 5/2002 | Dobrin et al. |
| 6,383,960 B1 | 5/2002 | Everett et al. |
| 6,394,989 B2 | 5/2002 | Mizutani |
| 6,402,729 B1 | 6/2002 | Boberg et al. |
| 6,402,731 B1 | 6/2002 | Suprise et al. |
| 6,403,857 B1 | 6/2002 | Gross et al. |
| 6,409,883 B1 | 6/2002 | Makolin |
| 6,410,820 B1 | 6/2002 | McFall et al. |
| 6,410,822 B1 | 6/2002 | Mizutani |
| 6,413,248 B1 | 7/2002 | Mizutani |
| 6,413,249 B1 | 7/2002 | Turi et al. |
| 6,414,214 B1 | 7/2002 | Engelhardt et al. |
| 6,419,667 B1 | 7/2002 | Avalon et al. |
| 6,423,046 B1 | 7/2002 | Fujioka et al. |
| 6,423,048 B1 | 7/2002 | Suzuki et al. |
| 6,423,884 B1 | 7/2002 | Oehmen |
| 6,429,350 B1 | 8/2002 | Tanzer et al. |
| 6,432,094 B1 | 8/2002 | Fujioka et al. |
| 6,432,098 B1 | 8/2002 | Kline et al. |
| 6,432,099 B2 | 8/2002 | Rönnberg |
| 6,437,214 B1 | 8/2002 | Everett et al. |
| 6,441,268 B1 | 8/2002 | Edwardsson |
| 6,443,933 B1 | 9/2002 | Suzuki et al. |
| 6,444,064 B1 | 9/2002 | Henry et al. |
| 6,447,496 B1 | 9/2002 | Mizutani |
| 6,458,111 B1 | 10/2002 | Onishi et al. |
| 6,458,877 B1 | 10/2002 | Ahmed et al. |
| 6,459,016 B1 | 10/2002 | Rosenfeld et al. |
| 6,461,342 B2 | 10/2002 | Tanji et al. |
| 6,461,343 B1 | 10/2002 | Schaefer et al. |
| 6,472,478 B1 | 10/2002 | Funk et al. |
| 6,475,201 B2 | 11/2002 | Saito et al. |
| 6,494,872 B1 | 12/2002 | Suzuki et al. |
| 6,494,873 B2 | 12/2002 | Karlsson et al. |
| 6,500,159 B1 | 12/2002 | Carvalho |
| 6,503,233 B1 | 1/2003 | Chen |
| 6,503,979 B1 | 1/2003 | Funk et al. |
| 6,506,186 B1 | 1/2003 | Roessler |
| 6,506,961 B1 | 1/2003 | Levy |
| 6,515,195 B1 | 2/2003 | Lariviere |
| 6,517,525 B1 | 2/2003 | Berthou |
| 6,518,479 B1 | 2/2003 | Graef |
| 6,520,947 B1 | 2/2003 | Tilly et al. |
| 6,521,811 B1 | 2/2003 | Lassen |
| 6,521,812 B1 | 2/2003 | Graef |
| 6,524,294 B1 | 2/2003 | Hilston et al. |

(56) References Cited

U.S. PATENT DOCUMENTS

| | | |
|---|---|---|
| 6,525,240 B1 | 2/2003 | Graef |
| 6,528,698 B2 * | 3/2003 | Mizutani et al. ............. 604/382 |
| 6,531,025 B1 | 3/2003 | Lender et al. |
| 6,531,027 B1 | 3/2003 | Lender et al. |
| 6,534,149 B1 | 3/2003 | Daley et al. |
| 6,559,081 B1 | 5/2003 | Erspamer |
| 6,559,239 B1 | 5/2003 | Riegel et al. |
| 6,562,168 B1 | 5/2003 | Schmitt et al. |
| 6,562,192 B1 | 5/2003 | Hamilton |
| 6,569,137 B2 | 5/2003 | Suzuki et al. |
| 6,573,422 B1 | 6/2003 | Rosenfeld |
| 6,585,713 B1 | 7/2003 | LaMahieu et al. |
| 6,585,858 B1 | 7/2003 | Otto et al. |
| 6,602,234 B2 | 8/2003 | Klemp et al. |
| 6,605,070 B2 | 8/2003 | Ludwig et al. |
| 6,605,172 B1 * | 8/2003 | Anderson et al. ............. 156/199 |
| 6,605,752 B2 | 8/2003 | Magnusson et al. |
| 6,610,900 B1 | 8/2003 | Tanzer |
| 6,630,054 B1 | 10/2003 | Graef |
| 6,632,209 B1 | 10/2003 | Chmielewski |
| 6,632,504 B1 | 10/2003 | Gillespie et al. |
| 6,645,569 B2 | 11/2003 | Cramer et al. |
| 6,646,180 B1 | 11/2003 | Chmielewski |
| 6,648,869 B1 | 11/2003 | Gillies et al. |
| 6,648,870 B2 | 11/2003 | Itoh et al. |
| 6,648,871 B2 | 11/2003 | Kusibojoska et al. |
| 6,649,807 B2 | 11/2003 | Mizutani |
| 6,649,810 B1 | 11/2003 | Minato et al. |
| 6,657,015 B1 | 12/2003 | Riegel et al. |
| 6,657,102 B2 | 12/2003 | Furuya |
| 6,667,424 B1 | 12/2003 | Hamilton |
| 6,670,522 B1 | 12/2003 | Graef |
| 6,673,982 B1 | 1/2004 | Chen |
| 6,673,983 B1 | 1/2004 | Graef |
| 6,673,985 B2 | 1/2004 | Mizutani |
| 6,682,515 B1 | 1/2004 | Mizutani et al. |
| 6,682,516 B2 | 1/2004 | Johnston |
| 6,689,115 B1 | 2/2004 | Popp et al. |
| 6,689,934 B2 | 2/2004 | Dodge, II et al. |
| 6,695,827 B2 | 2/2004 | Chen |
| 6,700,034 B1 | 3/2004 | Lindsay et al. |
| 6,703,538 B2 | 3/2004 | Lassen |
| 6,705,465 B2 | 3/2004 | Ling et al. |
| 6,706,943 B2 | 3/2004 | Onishi |
| 6,710,224 B2 | 3/2004 | Chmielewski et al. |
| 6,710,225 B1 | 3/2004 | Everett et al. |
| 6,716,205 B2 | 4/2004 | Popp et al. |
| 6,716,441 B1 | 4/2004 | Osborne et al. |
| 6,717,029 B2 | 4/2004 | Baker |
| 6,726,668 B2 | 4/2004 | Underhill et al. |
| 6,726,792 B1 | 4/2004 | Johnson et al. |
| 6,734,335 B1 | 5/2004 | Graef |
| 6,790,798 B1 | 9/2004 | Suzuki et al. |
| 6,809,158 B2 | 10/2004 | Ikeuchi et al. |
| 6,818,083 B2 | 11/2004 | Mcamish et al. |
| 6,830,800 B2 | 12/2004 | Curro et al. |
| 6,840,929 B2 | 1/2005 | Kurata |
| 6,846,374 B2 | 1/2005 | Popp |
| 6,858,771 B2 | 2/2005 | Yoshimasa |
| 6,863,933 B2 | 3/2005 | Cramer et al. |
| 6,863,960 B2 | 3/2005 | Curro et al. |
| 6,867,345 B2 | 3/2005 | Shimoe et al. |
| 6,867,346 B1 | 3/2005 | Dopps |
| 6,878,433 B2 | 4/2005 | Curro et al. |
| 6,880,211 B2 | 4/2005 | Jackson et al. |
| 6,891,080 B2 | 5/2005 | Minato |
| 6,904,865 B2 | 6/2005 | Klofta |
| 6,911,574 B1 | 6/2005 | Mizutani |
| 6,923,797 B2 | 8/2005 | Shinohara et al. |
| 6,926,703 B2 | 8/2005 | Sugito |
| 6,929,629 B2 | 8/2005 | Drevik et al. |
| 6,939,914 B2 | 9/2005 | Qin et al. |
| 6,946,585 B2 | 9/2005 | Brown |
| 6,953,451 B2 | 10/2005 | Berba |
| 6,955,733 B2 | 10/2005 | Henry et al. |
| 6,962,578 B1 | 11/2005 | Lavon |
| 6,962,645 B2 | 11/2005 | Graef |
| 6,965,058 B1 | 11/2005 | Raidel |
| 6,969,781 B2 | 11/2005 | Graef |
| 6,972,010 B2 | 12/2005 | Pesce et al. |
| 6,972,011 B2 * | 12/2005 | Maeda et al. ............. 604/385.01 |
| 7,001,167 B2 | 2/2006 | Venturino |
| 7,014,632 B2 | 3/2006 | Takino et al. |
| 7,015,370 B2 | 3/2006 | Watanabe |
| 7,037,299 B2 | 5/2006 | Turi et al. |
| 7,037,571 B2 | 5/2006 | Fish et al. |
| 7,048,726 B2 | 5/2006 | Kusagawa et al. |
| 7,056,311 B2 | 6/2006 | Kinoshita |
| 7,067,711 B2 | 6/2006 | Kinoshita et al. |
| 7,073,373 B2 | 7/2006 | La Fortune |
| 7,078,583 B2 | 7/2006 | Kudo |
| 7,090,665 B2 | 8/2006 | Ohashi |
| 7,108,759 B2 | 9/2006 | You |
| 7,108,916 B2 | 9/2006 | Ehrnsperger et al. |
| 7,112,621 B2 | 9/2006 | Rohrbaugh et al. |
| 7,122,713 B2 | 10/2006 | Komatsu |
| 7,125,470 B2 | 10/2006 | Graef |
| 7,132,585 B2 | 11/2006 | Kudo |
| 7,147,628 B2 | 12/2006 | Drevik |
| 7,150,729 B2 | 12/2006 | Shimada |
| 7,154,019 B2 | 12/2006 | Mishima et al. |
| 7,160,281 B2 | 1/2007 | Leminh et al. |
| 7,166,190 B2 | 1/2007 | Graef |
| 7,169,136 B2 | 1/2007 | Otsubo |
| 7,183,360 B2 | 2/2007 | Daniel et al. |
| 7,189,888 B2 | 3/2007 | Wang et al. |
| 7,196,241 B2 | 3/2007 | Kinoshita |
| 7,199,211 B2 | 4/2007 | Popp et al. |
| 7,204,830 B2 | 4/2007 | Mishima |
| 7,207,978 B2 | 4/2007 | Takino |
| 7,219,403 B2 | 5/2007 | Miyamoto et al. |
| 7,220,251 B2 | 5/2007 | Otsubo et al. |
| 7,250,481 B2 | 7/2007 | Jaworek et al. |
| 7,252,657 B2 | 8/2007 | Mishima |
| 7,265,258 B2 | 9/2007 | Hamilton |
| RE39,919 E | 11/2007 | Dodge, II et al. |
| 7,311,968 B2 | 12/2007 | Ehrnsperger et al. |
| 7,312,372 B2 | 12/2007 | Miyama |
| 7,318,820 B2 | 1/2008 | LaVon et al. |
| 7,329,244 B2 | 2/2008 | Otsubo |
| 7,329,246 B2 | 2/2008 | Kinoshita |
| 7,335,810 B2 | 2/2008 | Yoshimasa et al. |
| 7,377,914 B2 | 5/2008 | LaVon |
| 7,429,689 B2 | 9/2008 | Chen |
| 7,435,244 B2 | 10/2008 | Schroer et al. |
| 7,465,373 B2 | 12/2008 | Graef |
| 7,500,969 B2 | 3/2009 | Mishima |
| 7,504,552 B2 | 3/2009 | Tamura |
| 7,521,109 B2 | 4/2009 | Suzuki et al. |
| 7,521,587 B2 | 4/2009 | Busam et al. |
| 7,537,832 B2 | 5/2009 | Carlucci et al. |
| 7,547,815 B2 | 6/2009 | Ohashi |
| 7,550,646 B2 | 6/2009 | Tamura |
| 7,563,257 B2 | 7/2009 | Nakajima |
| 7,588,561 B2 | 9/2009 | Kenmochi |
| 7,594,904 B2 | 9/2009 | Rosenfeld |
| 7,625,363 B2 | 12/2009 | Yoshimasa |
| 7,641,642 B2 | 1/2010 | Murai et al. |
| 7,648,490 B2 | 1/2010 | Kuroda |
| 7,652,111 B2 | 1/2010 | Hermeling et al. |
| 7,666,173 B2 | 2/2010 | Mishima |
| 7,666,174 B2 | 2/2010 | Kawakami et al. |
| 7,686,790 B2 * | 3/2010 | Rasmussen et al. .......... 604/317 |
| 7,687,596 B2 | 3/2010 | Hermeling et al. |
| 7,695,461 B2 | 4/2010 | Rosenfeld |
| 7,696,402 B2 | 4/2010 | Nishikawa |
| 7,708,725 B2 | 5/2010 | Tamagawa |
| 7,717,150 B2 | 5/2010 | Manabe |
| 7,718,021 B2 | 5/2010 | Venturino et al. |
| 7,722,587 B2 | 5/2010 | Suzuki et al. |
| 7,722,590 B2 | 5/2010 | Tsuji |
| 7,727,217 B2 | 6/2010 | Hancock-Cooke |
| 7,736,351 B2 | 6/2010 | Nigam |
| 7,744,576 B2 | 6/2010 | Busam et al. |

(56) References Cited

U.S. PATENT DOCUMENTS

| | | |
|---|---|---|
| 7,744,578 B2 | 6/2010 | Tanio et al. |
| 7,750,203 B2 | 7/2010 | Busam et al. |
| 7,754,822 B2 | 7/2010 | Daniel et al. |
| 7,754,940 B2 | 7/2010 | Brisebois |
| 7,759,540 B2 | 7/2010 | Litvay et al. |
| 7,763,004 B2 | 7/2010 | Beck |
| 7,767,875 B2 | 8/2010 | Olson |
| 7,767,878 B2 | 8/2010 | Suzuki |
| 7,772,420 B2 | 8/2010 | Hermeling et al. |
| 7,786,341 B2 | 8/2010 | Schneider et al. |
| 7,795,492 B2 | 9/2010 | Vartiainen |
| 7,803,145 B2 | 9/2010 | Rosenfeld |
| 7,825,291 B2 * | 11/2010 | Elfsberg et al. ............... 604/378 |
| 7,850,672 B2 | 12/2010 | Guidotti et al. |
| 7,851,667 B2 | 12/2010 | Becker et al. |
| 7,855,314 B2 | 12/2010 | Hanao |
| 7,857,797 B2 | 12/2010 | Kudo |
| 7,858,842 B2 | 12/2010 | Komatsu |
| 7,884,259 B2 | 2/2011 | Hanao |
| 7,888,549 B2 | 2/2011 | Jansson et al. |
| 7,910,797 B2 | 3/2011 | Nandrea |
| 7,935,207 B2 | 5/2011 | Zhao |
| 7,935,861 B2 | 5/2011 | Suzuki |
| 7,938,813 B2 | 5/2011 | Wang et al. |
| 7,942,858 B2 | 5/2011 | Francoeur |
| 7,951,126 B2 | 5/2011 | Nanjyo |
| 7,982,091 B2 | 7/2011 | Konawa |
| 7,993,319 B2 | 8/2011 | Sperl |
| 8,017,827 B2 | 9/2011 | Hundorf et al. |
| 8,029,486 B2 | 10/2011 | Nakajima |
| 8,034,991 B2 | 10/2011 | Bruzadin et al. |
| 8,039,684 B2 | 10/2011 | Guidotti et al. |
| 8,052,454 B2 | 11/2011 | Polnyi |
| 8,057,620 B2 | 11/2011 | Perego et al. |
| 8,109,915 B2 | 2/2012 | Shimoe |
| 8,133,212 B2 | 3/2012 | Takada |
| 8,148,598 B2 | 4/2012 | Tsang et al. |
| 8,163,124 B2 | 4/2012 | Moriura et al. |
| 8,173,858 B2 | 5/2012 | Kuroda |
| 8,178,747 B2 | 5/2012 | Venturino et al. |
| 8,183,430 B2 | 5/2012 | Hakansson et al. |
| 8,186,296 B2 | 5/2012 | Brown et al. |
| 8,187,240 B2 | 5/2012 | Busam et al. |
| 8,198,506 B2 | 6/2012 | Venturino et al. |
| 8,211,815 B2 | 7/2012 | Baker |
| 8,236,715 B2 | 8/2012 | Schmidt et al. |
| 8,237,012 B2 | 8/2012 | Miyama |
| 8,246,594 B2 | 8/2012 | Sperl |
| 8,258,367 B2 | 9/2012 | Lawson et al. |
| 8,268,424 B1 | 9/2012 | Suzuki |
| 8,273,943 B2 | 9/2012 | Noda |
| 8,283,516 B2 | 10/2012 | Litvay |
| 8,317,766 B2 | 11/2012 | Naoto |
| 8,317,768 B2 | 11/2012 | Larsson |
| 8,319,005 B2 | 11/2012 | Becker et al. |
| 8,343,123 B2 | 1/2013 | Noda |
| 8,343,296 B2 * | 1/2013 | Blessing et al. ............... 156/209 |
| 8,361,047 B2 | 1/2013 | Mukai |
| 8,377,025 B2 | 2/2013 | Nakajima |
| 8,450,555 B2 | 5/2013 | Nhan et al. |
| 8,496,637 B2 | 7/2013 | Hundorf et al. |
| 8,519,213 B2 | 8/2013 | Venturino et al. |
| 8,524,355 B2 | 9/2013 | Nakaoka |
| 8,552,252 B2 | 10/2013 | Hundorf et al. |
| 8,568,566 B2 | 10/2013 | Jackels et al. |
| 8,581,019 B2 | 11/2013 | Carlucci et al. |
| 8,603,058 B2 | 12/2013 | Sperl et al. |
| 8,604,270 B2 | 12/2013 | Venturino et al. |
| 8,633,347 B2 | 1/2014 | Bianco et al. |
| 8,674,170 B2 | 3/2014 | Busam et al. |
| 8,766,031 B2 | 7/2014 | Becker et al. |
| 8,772,570 B2 | 7/2014 | Kawakami et al. |
| 8,785,715 B2 | 7/2014 | Wright et al. |
| 8,791,318 B2 | 7/2014 | Becker et al. |
| 2001/0007065 A1 | 7/2001 | Blanchard |
| 2001/0008964 A1 | 7/2001 | Kurata et al. |
| 2001/0016548 A1 | 8/2001 | Kugler et al. |
| 2001/0020157 A1 | 9/2001 | Mizutani |
| 2001/0037101 A1 | 11/2001 | Allan et al. |
| 2001/0044610 A1 | 11/2001 | Kim |
| 2002/0007167 A1 | 1/2002 | Dan |
| 2002/0007169 A1 | 1/2002 | Graef et al. |
| 2002/0016122 A1 | 2/2002 | Curro et al. |
| 2002/0016579 A1 | 2/2002 | Stenberg |
| 2002/0045881 A1 | 4/2002 | Kusibojoska et al. |
| 2002/0056516 A1 | 5/2002 | Ochi |
| 2002/0062112 A1 | 5/2002 | Mizutani |
| 2002/0062116 A1 | 5/2002 | Mizutani et al. |
| 2002/0065498 A1 | 5/2002 | Ohashi |
| 2002/0072471 A1 | 6/2002 | Ikeuchi et al. |
| 2002/0082575 A1 | 6/2002 | Dan |
| 2002/0087139 A1 | 7/2002 | Popp et al. |
| 2002/0102392 A1 | 8/2002 | Fish et al. |
| 2002/0115969 A1 * | 8/2002 | Maeda et al. ............... 604/368 |
| 2002/0123728 A1 | 9/2002 | Graef et al. |
| 2002/0151634 A1 | 10/2002 | Rohrbaugh et al. |
| 2002/0151861 A1 | 10/2002 | Klemp et al. |
| 2002/0173767 A1 | 11/2002 | Popp et al. |
| 2002/0192366 A1 | 12/2002 | Cramer et al. |
| 2003/0036741 A1 | 2/2003 | Abba et al. |
| 2003/0078553 A1 | 4/2003 | Wada |
| 2003/0084983 A1 | 5/2003 | Rangachari et al. |
| 2003/0088223 A1 | 5/2003 | Vogt et al. |
| 2003/0105190 A1 | 6/2003 | Diehl et al. |
| 2003/0114816 A1 | 6/2003 | Underhill |
| 2003/0114818 A1 | 6/2003 | Benecke et al. |
| 2003/0120235 A1 | 6/2003 | Boulanger |
| 2003/0135181 A1 | 7/2003 | Chen et al. |
| 2003/0135182 A1 | 7/2003 | Woon et al. |
| 2003/0139712 A1 | 7/2003 | Dodge |
| 2003/0139715 A1 | 7/2003 | Dodge |
| 2003/0139718 A1 | 7/2003 | Graef |
| 2003/0144642 A1 | 7/2003 | Dopps |
| 2003/0144644 A1 | 7/2003 | Murai et al. |
| 2003/0148684 A1 | 8/2003 | Cramer et al. |
| 2003/0148694 A1 | 8/2003 | Ghiam |
| 2003/0167045 A1 | 9/2003 | Graef |
| 2003/0171727 A1 | 9/2003 | Graef |
| 2003/0208175 A1 | 11/2003 | Gross |
| 2003/0225385 A1 | 12/2003 | Glaug |
| 2003/0233082 A1 | 12/2003 | Kline et al. |
| 2003/0236512 A1 | 12/2003 | Baker |
| 2004/0019338 A1 | 1/2004 | Litvay et al. |
| 2004/0022998 A1 | 2/2004 | Miyamoto et al. |
| 2004/0033750 A1 | 2/2004 | Everett |
| 2004/0063367 A1 | 4/2004 | Dodge |
| 2004/0064115 A1 | 4/2004 | Arora |
| 2004/0064116 A1 | 4/2004 | Arora |
| 2004/0064125 A1 | 4/2004 | Justmann et al. |
| 2004/0065420 A1 | 4/2004 | Graef |
| 2004/0082928 A1 | 4/2004 | Pesce et al. |
| 2004/0097895 A1 | 5/2004 | Busam et al. |
| 2004/0122411 A1 | 6/2004 | Hancock-Cooke |
| 2004/0127871 A1 | 7/2004 | Odorzynski |
| 2004/0127872 A1 | 7/2004 | Petryk |
| 2004/0134596 A1 | 7/2004 | Rosati et al. |
| 2004/0138633 A1 | 7/2004 | Mishima et al. |
| 2004/0147890 A1 | 7/2004 | Nakahata et al. |
| 2004/0158212 A1 | 8/2004 | Ponomarenko et al. |
| 2004/0162536 A1 | 8/2004 | Becker et al. |
| 2004/0167486 A1 | 8/2004 | Busam et al. |
| 2004/0167489 A1 | 8/2004 | Kellenberger et al. |
| 2004/0193127 A1 | 9/2004 | Hansson |
| 2004/0215160 A1 | 10/2004 | Chmielewski |
| 2004/0220541 A1 | 11/2004 | Suzuki et al. |
| 2004/0225271 A1 | 11/2004 | Datta et al. |
| 2004/0231065 A1 | 11/2004 | Daniel et al. |
| 2004/0236299 A1 | 11/2004 | Tsang et al. |
| 2004/0249355 A1 | 12/2004 | Tanio et al. |
| 2004/0260259 A1 | 12/2004 | Baker |
| 2005/0004543 A1 | 1/2005 | Schroer et al. |
| 2005/0004548 A1 | 1/2005 | Otsubo et al. |
| 2005/0008839 A1 | 1/2005 | Cramer et al. |
| 2005/0038401 A1 | 2/2005 | Suzuki et al. |

(56) References Cited

U.S. PATENT DOCUMENTS

| | | |
|---|---|---|
| 2005/0070867 A1 | 3/2005 | Beruda et al. |
| 2005/0085784 A1 | 4/2005 | LeMinh et al. |
| 2005/0090789 A1 | 4/2005 | Graef |
| 2005/0096615 A1* | 5/2005 | Kuen .................. A61F 13/536 604/385.01 |
| 2005/0109442 A1 | 5/2005 | Neubauer et al. |
| 2005/0137543 A1 | 6/2005 | Underhill et al. |
| 2005/0148258 A1 | 7/2005 | Chakravarty |
| 2005/0148990 A1 | 7/2005 | Shimoe |
| 2005/0154363 A1 | 7/2005 | Minato |
| 2005/0159720 A1 | 7/2005 | Gentilcore |
| 2005/0165208 A1 | 7/2005 | Popp et al. |
| 2005/0171499 A1 | 8/2005 | Nigam et al. |
| 2005/0176910 A1 | 8/2005 | Jaworek et al. |
| 2005/0203475 A1 | 9/2005 | LaVon et al. |
| 2005/0215752 A1 | 9/2005 | Popp et al. |
| 2005/0229543 A1 | 10/2005 | Tippey |
| 2005/0245684 A1 | 11/2005 | Daniel et al. |
| 2005/0288645 A1 | 12/2005 | LaVon |
| 2005/0288646 A1 | 12/2005 | LaVon |
| 2006/0004334 A1 | 1/2006 | Schlinz et al. |
| 2006/0021695 A1 | 2/2006 | Blessing et al. |
| 2006/0024433 A1 | 2/2006 | Blessing et al. |
| 2006/0069371 A1 | 3/2006 | Ohashi et al. |
| 2006/0073969 A1 | 4/2006 | Torli et al. |
| 2006/0081348 A1 | 4/2006 | Graef |
| 2006/0129114 A1 | 6/2006 | Mason et al. |
| 2006/0142724 A1 | 6/2006 | Watanabe |
| 2006/0155057 A1 | 7/2006 | Hermeling et al. |
| 2006/0155254 A1 | 7/2006 | Sanz et al. |
| 2006/0167215 A1 | 7/2006 | Hermeling et al. |
| 2006/0177647 A1 | 8/2006 | Schmidt et al. |
| 2006/0178071 A1 | 8/2006 | Schmidt et al. |
| 2006/0184146 A1 | 8/2006 | Suzuki |
| 2006/0184149 A1 | 8/2006 | Kasai et al. |
| 2006/0189954 A1 | 8/2006 | Kudo |
| 2006/0202380 A1 | 9/2006 | Bentley |
| 2006/0206091 A1 | 9/2006 | Cole |
| 2006/0211828 A1 | 9/2006 | Daniel et al. |
| 2006/0240229 A1 | 10/2006 | Ehrnsperger et al. |
| 2006/0264860 A1 | 11/2006 | Beck |
| 2006/0264861 A1 | 11/2006 | Lavon et al. |
| 2007/0027436 A1 | 2/2007 | Nakagawa et al. |
| 2007/0032770 A1 | 2/2007 | LaVon et al. |
| 2007/0043191 A1 | 2/2007 | Hermeling et al. |
| 2007/0043330 A1 | 2/2007 | Lankhof et al. |
| 2007/0073253 A1 | 3/2007 | Miyama |
| 2007/0078422 A1 | 4/2007 | Glaug et al. |
| 2007/0088308 A1 | 4/2007 | Ehrnsperger et al. |
| 2007/0093164 A1 | 4/2007 | Nakaoka |
| 2007/0093767 A1 | 4/2007 | Carlucci et al. |
| 2007/0100307 A1 | 5/2007 | Nomoto |
| 2007/0118087 A1 | 5/2007 | Flohr et al. |
| 2007/0123834 A1 | 5/2007 | McDowall et al. |
| 2007/0156108 A1 | 7/2007 | Becker et al. |
| 2007/0156110 A1 | 7/2007 | Thyfault |
| 2007/0167928 A1 | 7/2007 | Becker et al. |
| 2007/0179464 A1 | 8/2007 | Becker et al. |
| 2007/0179469 A1 | 8/2007 | Takahashi et al. |
| 2007/0191798 A1 | 8/2007 | Glaug |
| 2007/0219521 A1 | 9/2007 | Hird et al. |
| 2007/0219523 A1 | 9/2007 | Bruun |
| 2007/0244455 A1 | 10/2007 | Hansson et al. |
| 2007/0246147 A1 | 10/2007 | Venturino et al. |
| 2007/0282288 A1 | 12/2007 | Noda |
| 2007/0282290 A1 | 12/2007 | Cole |
| 2007/0282291 A1 | 12/2007 | Cole |
| 2008/0027402 A1 | 1/2008 | Schmidt et al. |
| 2008/0032035 A1 | 2/2008 | Schmidt et al. |
| 2008/0091159 A1 | 4/2008 | Carlucci et al. |
| 2008/0119810 A1 | 5/2008 | Kuroda |
| 2008/0125735 A1 | 5/2008 | Busam et al. |
| 2008/0221538 A1 | 9/2008 | Zhao |
| 2008/0221539 A1 | 9/2008 | Zhao |
| 2008/0228158 A1 | 9/2008 | Sue et al. |
| 2008/0262459 A1 | 10/2008 | Kamoto |
| 2008/0268194 A1 | 10/2008 | Kim et al. |
| 2008/0274227 A1 | 11/2008 | Boatman et al. |
| 2008/0281287 A1 | 11/2008 | Marcelo |
| 2008/0294140 A1 | 11/2008 | Ecker et al. |
| 2008/0312617 A1 | 12/2008 | Hundorf et al. |
| 2008/0312618 A1 | 12/2008 | Hundorf et al. |
| 2008/0312619 A1 | 12/2008 | Hundorf et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312623 A1 | 12/2008 | Hundorf et al. |
| 2008/0312624 A1 | 12/2008 | Hundorf et al. |
| 2008/0312625 A1 | 12/2008 | Hundorf et al. |
| 2008/0312627 A1 | 12/2008 | Takeuchi |
| 2008/0312628 A1 | 12/2008 | Hundorf et al. |
| 2009/0023848 A1 | 1/2009 | Ahmed et al. |
| 2009/0056867 A1* | 3/2009 | Moriura et al. ............... 156/276 |
| 2009/0062760 A1 | 3/2009 | Wright et al. |
| 2009/0112173 A1 | 4/2009 | Bissah |
| 2009/0112175 A1 | 4/2009 | Bissah et al. |
| 2009/0157022 A1 | 6/2009 | Macdonald |
| 2009/0192035 A1 | 7/2009 | Stueven et al. |
| 2009/0240220 A1 | 9/2009 | Macdonald |
| 2009/0247977 A1 | 10/2009 | Takeuchi |
| 2009/0258994 A1 | 10/2009 | Stueven et al. |
| 2009/0270825 A1 | 10/2009 | Wciorka et al. |
| 2009/0298963 A1 | 12/2009 | Matsumoto et al. |
| 2009/0299312 A1 | 12/2009 | Macdonald |
| 2009/0306618 A1 | 12/2009 | Kudo |
| 2009/0318884 A1 | 12/2009 | Meyer et al. |
| 2010/0051166 A1* | 3/2010 | Hundorf et al. ............... 156/62.8 |
| 2010/0062165 A1 | 3/2010 | Suzuki |
| 2010/0062934 A1 | 3/2010 | Suzuki |
| 2010/0063470 A1 | 3/2010 | Suzuki |
| 2010/0068520 A1 | 3/2010 | Stueven et al. |
| 2010/0100065 A1 | 4/2010 | Bianco |
| 2010/0121296 A1 | 5/2010 | Noda |
| 2010/0137773 A1 | 6/2010 | Gross |
| 2010/0137823 A1 | 6/2010 | Corneliusson |
| 2010/0198179 A1 | 8/2010 | Noda |
| 2010/0228210 A1 | 9/2010 | Busam et al. |
| 2010/0241097 A1 | 9/2010 | Nigam et al. |
| 2010/0262099 A1 | 10/2010 | Klofta |
| 2010/0274208 A1 | 10/2010 | Gabrielii |
| 2010/0274210 A1 | 10/2010 | Noda |
| 2010/0312208 A1 | 12/2010 | Bond et al. |
| 2010/0324521 A1 | 12/2010 | Mukai |
| 2010/0324523 A1 | 12/2010 | Mukai |
| 2010/0331801 A1 | 12/2010 | Kawakami et al. |
| 2011/0041999 A1 | 2/2011 | Hundorf et al. |
| 2011/0060303 A1 | 3/2011 | Bissah |
| 2011/0066127 A1 | 3/2011 | Kuwano |
| 2011/0071486 A1 | 3/2011 | Harada |
| 2011/0092944 A1 | 4/2011 | Sagisaka |
| 2011/0112498 A1 | 5/2011 | Nhan et al. |
| 2011/0125120 A1 | 5/2011 | Nishitani |
| 2011/0130732 A1 | 6/2011 | Jackels et al. |
| 2011/0130737 A1 | 6/2011 | Sagisaka |
| 2011/0137276 A1 | 6/2011 | Yoshikawa |
| 2011/0144602 A1 | 6/2011 | Long |
| 2011/0144604 A1 | 6/2011 | Noda |
| 2011/0144606 A1 | 6/2011 | Nandrea |
| 2011/0152813 A1 | 6/2011 | Ellingson |
| 2011/0166540 A1 | 7/2011 | Yang et al. |
| 2011/0172630 A1 | 7/2011 | Nomoto |
| 2011/0174430 A1 | 7/2011 | Zhao |
| 2011/0208147 A1 | 8/2011 | Kawakami et al. |
| 2011/0250413 A1 | 10/2011 | Lu et al. |
| 2011/0268932 A1 | 11/2011 | Catalan et al. |
| 2011/0274834 A1 | 11/2011 | Brown et al. |
| 2011/0288513 A1 | 11/2011 | Hundorf et al. |
| 2011/0288514 A1 | 11/2011 | Kuroda |
| 2011/0319846 A1 | 12/2011 | Rinnert et al. |
| 2011/0319848 A1 | 12/2011 | McKiernan et al. |
| 2011/0319851 A1 | 12/2011 | Kudo |
| 2012/0004633 A1 | 1/2012 | Marcelo |
| 2012/0016326 A1 | 1/2012 | Brennan et al. |
| 2012/0022479 A1 | 1/2012 | Cotton |

(56) References Cited

U.S. PATENT DOCUMENTS

| | | |
|---|---|---|
| 2012/0035566 A1 | 2/2012 | Sagisaka |
| 2012/0035576 A1 | 2/2012 | Ichikawa |
| 2012/0064792 A1 | 3/2012 | Bauduin |
| 2012/0071848 A1 | 3/2012 | Zhang |
| 2012/0165771 A1 | 6/2012 | Ruman et al. |
| 2012/0165776 A1 | 6/2012 | McGregor et al. |
| 2012/0175056 A1 | 7/2012 | Tsang |
| 2012/0184934 A1 | 7/2012 | Venturino |
| 2012/0232514 A1 | 9/2012 | Baker |
| 2012/0238977 A1 | 9/2012 | Oku |
| 2012/0253306 A1 | 10/2012 | Otsubo |
| 2012/0256750 A1 | 10/2012 | Novak |
| 2012/0270715 A1 | 10/2012 | Motegi et al. |
| 2012/0271262 A1 | 10/2012 | Venturino |
| 2012/0312491 A1 | 12/2012 | Jackels et al. |
| 2012/0316046 A1 | 12/2012 | Jackels et al. |
| 2012/0316523 A1 | 12/2012 | Hippe et al. |
| 2012/0316526 A1 | 12/2012 | Rosati et al. |
| 2012/0316527 A1 | 12/2012 | Rosati et al. |
| 2012/0316528 A1 | 12/2012 | Kreuzer et al. |
| 2012/0316529 A1 | 12/2012 | Kreuzer et al. |
| 2012/0323195 A1 | 12/2012 | Ehrnsperger et al. |
| 2012/0323201 A1 | 12/2012 | Bissah |
| 2012/0323202 A1 | 12/2012 | Bissah |
| 2013/0035656 A1 | 2/2013 | Moriya et al. |
| 2013/0041334 A1 | 2/2013 | Prioleau |
| 2013/0211354 A1 | 8/2013 | Tsuji et al. |
| 2013/0218115 A1 | 8/2013 | Katsuragawa et al. |
| 2013/0226119 A1 | 8/2013 | Katsuragawa et al. |
| 2013/0226120 A1 | 8/2013 | Van De Maele |
| 2014/0005622 A1 | 1/2014 | Wirtz et al. |
| 2014/0005623 A1 | 1/2014 | Wirtz et al. |
| 2014/0027066 A1 | 1/2014 | Jackels et al. |
| 2014/0039437 A1 | 1/2014 | Van De Maele |
| 2014/0045683 A1 | 2/2014 | Loick et al. |
| 2014/0135726 A1 | 5/2014 | Busam et al. |
| 2014/0142531 A1 | 5/2014 | Sasayama et al. |
| 2014/0163500 A1 | 6/2014 | Roe et al. |
| 2014/0163501 A1 | 6/2014 | Ehrnsperger et al. |
| 2014/0163502 A1 | 6/2014 | Arizti et al. |
| 2014/0163503 A1 | 6/2014 | Arizti et al. |
| 2014/0163506 A1 | 6/2014 | Roe et al. |
| 2014/0163511 A1 | 6/2014 | Roe et al. |
| 2014/0324007 A1 | 10/2014 | Hundorf et al. |
| 2014/0324008 A1 | 10/2014 | Hundorf et al. |

FOREIGN PATENT DOCUMENTS

| | | |
|---|---|---|
| CA | 2308961 | 11/2000 |
| CA | 2487027 | 12/2003 |
| CA | 2561521 | 3/2007 |
| CA | 2630713 | 11/2008 |
| CA | 2636673 | 1/2009 |
| CA | 2712563 | 8/2010 |
| CA | 2702001 | 10/2010 |
| CN | 1238171 A | 12/1999 |
| CN | 2362468 Y | 2/2000 |
| CN | 2527254 Y | 12/2002 |
| CN | 2535020 Y | 2/2003 |
| CN | 2548609 Y | 5/2003 |
| CN | 1539391 | 10/2004 |
| CN | 1939242 | 4/2007 |
| CN | 101292930 | 10/2008 |
| CN | 201263750 | 7/2009 |
| CN | 201591689 | 9/2010 |
| CN | 201855366 U | 6/2011 |
| DE | 3205931 C2 | 9/1983 |
| DE | 3608114 A1 | 9/1987 |
| DE | 19732499 | 2/1999 |
| DE | 10204937 A1 | 8/2003 |
| EP | 083022 | 7/1983 |
| EP | 149880 | 7/1985 |
| EP | 0149880 A2 | 7/1985 |
| EP | 0203289 A2 | 12/1986 |
| EP | 0206208 | 12/1986 |
| EP | 209561 B1 | 1/1987 |
| EP | 0 226 939 A1 | 7/1987 |
| EP | 297411 B1 | 1/1989 |
| EP | 304957 | 3/1989 |
| EP | 374542 | 6/1990 |
| EP | 394274 | 10/1990 |
| EP | 0403832 | 12/1990 |
| EP | 481322 B1 | 4/1992 |
| EP | 530438 | 3/1993 |
| EP | 547847 | 6/1993 |
| EP | 555346 | 8/1993 |
| EP | 559476 | 9/1993 |
| EP | 591647 B2 | 4/1994 |
| EP | 597273 B1 | 5/1994 |
| EP | 601610 B2 | 6/1994 |
| EP | 632068 | 1/1995 |
| EP | 0640330 A1 | 3/1995 |
| EP | 0668066 | 9/1995 |
| EP | 685214 | 12/1995 |
| EP | 687453 | 12/1995 |
| EP | 0 691 133 A1 | 1/1996 |
| EP | 0689817 | 1/1996 |
| EP | 0 700 673 A1 | 3/1996 |
| EP | 724418 | 8/1996 |
| EP | 725613 | 8/1996 |
| EP | 725615 | 8/1996 |
| EP | 725616 | 8/1996 |
| EP | 758543 | 2/1997 |
| EP | 0761194 | 3/1997 |
| EP | 769284 | 4/1997 |
| EP | 0781537 | 7/1997 |
| EP | 783877 B1 | 7/1997 |
| EP | 787472 | 8/1997 |
| EP | 788874 B1 | 8/1997 |
| EP | 796068 | 9/1997 |
| EP | 799004 | 10/1997 |
| EP | 822794 B1 | 2/1998 |
| EP | 826351 | 3/1998 |
| EP | 844861 | 6/1998 |
| EP | 863733 | 9/1998 |
| EP | 971751 | 9/1998 |
| EP | 875224 A1 | 11/1998 |
| EP | 880955 | 12/1998 |
| EP | 891758 | 1/1999 |
| EP | 0893115 | 1/1999 |
| EP | 904755 | 3/1999 |
| EP | 0916327 | 5/1999 |
| EP | 925769 A2 | 6/1999 |
| EP | 933074 | 8/1999 |
| EP | 937736 | 8/1999 |
| EP | 941157 | 9/1999 |
| EP | 947549 | 10/1999 |
| EP | 951887 B1 | 10/1999 |
| EP | 0951890 | 10/1999 |
| EP | 2295493 | 10/1999 |
| EP | 2305749 | 10/1999 |
| EP | 2330152 | 10/1999 |
| EP | 953326 | 11/1999 |
| EP | 0978263 A1 | 2/2000 |
| EP | 985397 B1 | 3/2000 |
| EP | 1005847 | 6/2000 |
| EP | 1008333 | 6/2000 |
| EP | 1013252 B1 | 6/2000 |
| EP | 1018999 | 7/2000 |
| EP | 1019002 B1 | 7/2000 |
| EP | 1019003 B1 | 7/2000 |
| EP | 1022008 | 7/2000 |
| EP | 1023884 | 8/2000 |
| EP | 1053729 | 11/2000 |
| EP | 1059072 A2 | 12/2000 |
| EP | 1063954 | 1/2001 |
| EP | 1071388 | 1/2001 |
| EP | 1078618 | 2/2001 |
| EP | 1088537 A2 | 4/2001 |
| EP | 1116479 A2 | 7/2001 |
| EP | 1132069 | 9/2001 |
| EP | 1173128 | 1/2002 |
| EP | 1175194 B1 | 1/2002 |
| EP | 1184018 | 3/2002 |

(56) References Cited

FOREIGN PATENT DOCUMENTS

| | | |
|---|---|---|
| EP | 1192312 B1 | 4/2002 |
| EP | 1196122 B2 | 4/2002 |
| EP | 1199059 | 4/2002 |
| EP | 1199327 | 4/2002 |
| EP | 1208824 | 5/2002 |
| EP | 0793469 | 6/2002 |
| EP | 1210925 | 6/2002 |
| EP | 1224922 | 7/2002 |
| EP | 1225857 | 7/2002 |
| EP | 1262531 A1 | 12/2002 |
| EP | 1263374 B1 | 12/2002 |
| EP | 1275358 | 1/2003 |
| EP | 1275361 | 1/2003 |
| EP | 1293187 | 3/2003 |
| EP | 1304986 B1 | 5/2003 |
| EP | 1332742 B1 | 8/2003 |
| EP | 1339368 | 9/2003 |
| EP | 1374817 | 1/2004 |
| EP | 1388334 | 2/2004 |
| EP | 1402863 | 3/2004 |
| EP | 962208 | 8/2004 |
| EP | 1447066 | 8/2004 |
| EP | 1447067 | 8/2004 |
| EP | 1460987 | 9/2004 |
| EP | 963749 | 11/2004 |
| EP | 1495739 | 1/2005 |
| EP | 1524955 | 4/2005 |
| EP | 1920743 | 4/2005 |
| EP | 1541103 | 6/2005 |
| EP | 1551344 | 7/2005 |
| EP | 1586289 | 10/2005 |
| EP | 1588723 | 10/2005 |
| EP | 1605882 | 12/2005 |
| EP | 1609448 | 12/2005 |
| EP | 1 621 166 A1 | 2/2006 |
| EP | 1621166 A1 * | 2/2006 |
| EP | 1621167 | 2/2006 |
| EP | 1632206 | 3/2006 |
| EP | 1642556 | 4/2006 |
| EP | 1656162 | 5/2006 |
| EP | 1669046 | 6/2006 |
| EP | 1688114 | 8/2006 |
| EP | 2314265 | 8/2006 |
| EP | 1723939 | 11/2006 |
| EP | 1738727 | 1/2007 |
| EP | 1754461 | 2/2007 |
| EP | 1787611 | 5/2007 |
| EP | 1813238 | 8/2007 |
| EP | 2008626 | 12/2008 |
| EP | 2055279 A1 | 5/2009 |
| EP | 2093049 | 8/2009 |
| EP | 2130522 | 12/2009 |
| EP | 2444046 | 4/2012 |
| EP | 2532329 A1 | 12/2012 |
| EP | 2532332 A1 | 12/2012 |
| EP | 2679210 A1 | 1/2014 |
| EP | 2740449 | 6/2014 |
| EP | 2740450 | 6/2014 |
| EP | 2740452 | 6/2014 |
| ES | 2213491 | 8/2004 |
| ET | 1669046 | 6/2006 |
| FR | 2566631 | 1/1986 |
| FR | 2612770 | 9/1988 |
| FR | 2810234 | 12/2001 |
| GB | 1333081 A | 8/1971 |
| GB | 1307441 | 2/1973 |
| GB | 1513055 | 6/1978 |
| GB | 2101468 | 1/1983 |
| GB | 2170108 | 7/1986 |
| GB | 2262873 | 7/1993 |
| GB | 2288540 A | 6/1994 |
| GB | 2354449 | 3/2001 |
| GB | 2452260 A | 10/2007 |
| GR | 851769 | 11/1985 |
| IN | 0984/KOL/1999 | 10/2005 |
| IN | 212479 B | 3/2007 |
| IN | 208543 B | 8/2007 |
| IN | 0980/MUM/2009 | 6/2009 |
| JP | 55-72928 U | 5/1980 |
| JP | 59-8322 U | 1/1984 |
| JP | 63-0148323 U | 9/1988 |
| JP | 03-224481 B2 | 10/1991 |
| JP | 04-122256 | 4/1992 |
| JP | 06-269475 A | 9/1994 |
| JP | 11-033056 A | 2/1999 |
| JP | 11-318980 | 11/1999 |
| JP | 2000-232985 | 8/2000 |
| JP | 2000-238161 | 9/2000 |
| JP | 2001-037810 | 2/2001 |
| JP | 2001-046435 A | 2/2001 |
| JP | 2001-120597 | 5/2001 |
| JP | 2001-158074 | 6/2001 |
| JP | 2001-178768 A | 7/2001 |
| JP | 2001-198157 | 7/2001 |
| JP | 2001-224626 A | 8/2001 |
| JP | 03-420481 B2 | 11/2001 |
| JP | 2001-353174 A | 12/2001 |
| JP | 2002-052042 A | 2/2002 |
| JP | 2002-113800 A | 4/2002 |
| JP | 2002-165832 | 6/2002 |
| JP | 2002-165836 | 6/2002 |
| JP | 2002-272769 A | 9/2002 |
| JP | 2002-325792 A | 11/2002 |
| JP | 2002-325799 A | 11/2002 |
| JP | 2002-369841 A | 12/2002 |
| JP | 2003-153955 A | 5/2003 |
| JP | 2003-265524 A | 9/2003 |
| JP | 2003-275237 | 9/2003 |
| JP | 2004-089269 | 3/2004 |
| JP | 03-566012 B2 | 6/2004 |
| JP | 03-568146 B2 | 6/2004 |
| JP | 03-616077 B2 | 11/2004 |
| JP | 2004-337314 A | 12/2004 |
| JP | 2004-337385 A | 12/2004 |
| JP | 03-640475 B2 | 1/2005 |
| JP | 2005-000312 A | 1/2005 |
| JP | 03-660816 B2 | 3/2005 |
| JP | 03-676219 B2 | 5/2005 |
| JP | 03-688403 B2 | 6/2005 |
| JP | 03-705943 B2 | 8/2005 |
| JP | 03-719819 B2 | 9/2005 |
| JP | 03-724963 B2 | 9/2005 |
| JP | 03-725008 B2 | 9/2005 |
| JP | 03-737376 B2 | 11/2005 |
| JP | 2006-014792 A | 1/2006 |
| JP | 03-781617 B2 | 3/2006 |
| JP | 2006-110329 | 4/2006 |
| JP | 03-801449 B2 | 5/2006 |
| JP | 2006-116036 A | 5/2006 |
| JP | 03-850102 B2 | 9/2006 |
| JP | 03-850207 B2 | 9/2006 |
| JP | 03-856941 B2 | 9/2006 |
| JP | 03-868628 B2 | 10/2006 |
| JP | 03-874499 B2 | 11/2006 |
| JP | 03-877702 B2 | 11/2006 |
| JP | 2006-325639 A | 12/2006 |
| JP | 2006-346021 | 12/2006 |
| JP | 03-904356 B2 | 1/2007 |
| JP | 2007-007455 A | 1/2007 |
| JP | 2007-007456 A | 1/2007 |
| JP | 03-926042 B2 | 3/2007 |
| JP | 03-934855 B2 | 3/2007 |
| JP | 2007-089906 A | 4/2007 |
| JP | 2007-105198 A | 4/2007 |
| JP | 2007-152033 A | 6/2007 |
| JP | 03-986210 B2 | 7/2007 |
| JP | 03-986222 B2 | 7/2007 |
| JP | 2007-167453 | 7/2007 |
| JP | 2007-175515 A | 7/2007 |
| JP | 2007-195665 A | 8/2007 |
| JP | 2007-267763 A | 10/2007 |
| JP | 2007-275491 A | 10/2007 |
| JP | 04-035341 B2 | 11/2007 |
| JP | 04-058281 B2 | 12/2007 |

(56) References Cited

FOREIGN PATENT DOCUMENTS

| | | |
|---|---|---|
| JP | 04-061086 B2 | 12/2007 |
| JP | 04-092319 B2 | 3/2008 |
| JP | 2008-080150 A | 4/2008 |
| JP | 2008-093289 A | 4/2008 |
| JP | 04-124322 B2 | 5/2008 |
| JP | 2008-119081 A | 5/2008 |
| JP | 2008-136739 A | 6/2008 |
| JP | 2008-136877 A | 6/2008 |
| JP | 04-148594 B2 | 7/2008 |
| JP | 04-148620 B2 | 7/2008 |
| JP | 2008-154606 A | 7/2008 |
| JP | 04-162609 B2 | 8/2008 |
| JP | 04-162637 B2 | 8/2008 |
| JP | 04-166923 B2 | 8/2008 |
| JP | 04-167406 B2 | 8/2008 |
| JP | 04-173723 B2 | 8/2008 |
| JP | 04-190675 B2 | 9/2008 |
| JP | 04-190693 B2 | 9/2008 |
| JP | 04-208338 B2 | 10/2008 |
| JP | 2008-246089 | 10/2008 |
| JP | 04-230971 B2 | 12/2008 |
| JP | 2008-295475 A | 12/2008 |
| JP | 2008-295713 A | 12/2008 |
| JP | 04-261593 B2 | 2/2009 |
| JP | 2009-112590 | 5/2009 |
| JP | 04-322228 B2 | 6/2009 |
| JP | 2009-136601 | 6/2009 |
| JP | 2009-142401 A | 7/2009 |
| JP | 2009-201878 A | 9/2009 |
| JP | 04-392936 B2 | 10/2009 |
| JP | 2009-232987 A | 10/2009 |
| JP | 2009-261777 A | 11/2009 |
| JP | 2009-291473 A | 12/2009 |
| JP | 2009-297048 A | 12/2009 |
| JP | 04-458702 B2 | 2/2010 |
| JP | 04-459013 B2 | 2/2010 |
| JP | 2010-022560 | 2/2010 |
| JP | 04-481325 B2 | 3/2010 |
| JP | 2010-051654 A | 3/2010 |
| JP | 2010-063814 A | 3/2010 |
| JP | 2010-063944 A | 3/2010 |
| JP | 04-492957 B2 | 4/2010 |
| JP | 2010-068954 A | 4/2010 |
| JP | 2010-075462 A | 4/2010 |
| JP | 2010-082059 A | 4/2010 |
| JP | 2010-104545 A | 5/2010 |
| JP | 2010-104547 A | 5/2010 |
| JP | 2010-110535 A | 5/2010 |
| JP | 2010-119454 A | 6/2010 |
| JP | 2010-119605 A | 6/2010 |
| JP | 2010-119743 A | 6/2010 |
| JP | 2010-131131 A | 6/2010 |
| JP | 2010-131132 A | 6/2010 |
| JP | 2010-131206 | 6/2010 |
| JP | 2010-131297 A | 6/2010 |
| JP | 2010-136917 A | 6/2010 |
| JP | 2010-136973 A | 6/2010 |
| JP | 04-540563 B2 | 7/2010 |
| JP | 04-587947 B2 | 9/2010 |
| JP | 2010-194124 A | 9/2010 |
| JP | 2010-201093 | 9/2010 |
| JP | 2010-221067 | 10/2010 |
| JP | 04-620299 B2 | 11/2010 |
| JP | 04-627472 B2 | 11/2010 |
| JP | 04-627473 B2 | 11/2010 |
| JP | 04-638087 B2 | 12/2010 |
| JP | 04-652626 B2 | 12/2010 |
| JP | 2010-273842 A | 12/2010 |
| JP | 2010-284418 A | 12/2010 |
| JP | 2010/284418 A | 12/2010 |
| JP | 2011-000480 A | 1/2011 |
| JP | 2011-030700 | 2/2011 |
| JP | 04-693574 B2 | 3/2011 |
| JP | 2011-067484 A | 4/2011 |
| JP | 2011-072720 A | 4/2011 |
| JP | 2011-104014 | 6/2011 |
| JP | 2011-104122 A | 6/2011 |
| JP | 2011-120661 A | 6/2011 |
| JP | 2011-125360 A | 6/2011 |
| JP | 2011-125537 | 6/2011 |
| JP | 04-776516 B2 | 7/2011 |
| JP | 2011-130797 A | 7/2011 |
| JP | 2011-130799 A | 7/2011 |
| JP | 2011-156032 A | 8/2011 |
| JP | 2011-156070 A | 8/2011 |
| JP | 2011-156254 | 8/2011 |
| JP | 04-824882 B2 | 9/2011 |
| JP | 48-50272 B2 | 10/2011 |
| JP | 04-855533 B2 | 11/2011 |
| JP | 2011-239858 | 12/2011 |
| JP | 04-931572 B2 | 2/2012 |
| JP | 04-937225 B2 | 3/2012 |
| JP | 04-953618 B2 | 3/2012 |
| JP | 04-969437 B2 | 4/2012 |
| JP | 04-969640 B2 | 4/2012 |
| JP | 04-974524 B2 | 4/2012 |
| JP | 04-979780 B2 | 4/2012 |
| JP | 49-71491 B2 | 4/2012 |
| JP | 05-016020 B2 | 6/2012 |
| JP | 05-027364 B2 | 6/2012 |
| JP | 05-031082 B2 | 7/2012 |
| JP | 05-042351 B2 | 7/2012 |
| JP | 05-043569 B2 | 7/2012 |
| JP | 05-043591 B2 | 7/2012 |
| JP | 05-046488 B2 | 7/2012 |
| JP | 2012-125625 A | 7/2012 |
| JP | 05-053765 B2 | 8/2012 |
| JP | 05-070275 B2 | 8/2012 |
| JP | 05-079931 B1 | 9/2012 |
| JP | 05-080189 B2 | 9/2012 |
| JP | 05-084442 B2 | 9/2012 |
| JP | 05-084476 B2 | 9/2012 |
| JP | 05-089269 B2 | 9/2012 |
| JP | 50-85770 B2 | 9/2012 |
| JP | 05-113146 B2 | 10/2012 |
| JP | 05-129536 B2 | 11/2012 |
| JP | 05-105884 B2 | 12/2012 |
| KR | 20010005620 | 1/2001 |
| KR | 20020035634 | 5/2002 |
| KR | 20080028771 | 4/2008 |
| SE | 9400916 | 3/1994 |
| SE | 9704893 | 12/1997 |
| WO | WO90/15830 | 12/1990 |
| WO | WO93/21237 | 10/1993 |
| WO | WO93/21879 | 11/1993 |
| WO | WO95/32698 | 2/1995 |
| WO | WO95/10996 | 4/1995 |
| WO | WO95/11652 | 5/1995 |
| WO | WO95/14453 | 6/1995 |
| WO | WO95/15139 | 6/1995 |
| WO | WO95/16424 | 6/1995 |
| WO | WO95/16746 | 6/1995 |
| WO | WO95/19753 | 7/1995 |
| WO | WO95/21596 | 8/1995 |
| WO | WO95/24173 | 9/1995 |
| WO | WO95/29657 | 11/1995 |
| WO | WO95/32698 | 12/1995 |
| WO | WO95/34329 | 12/1995 |
| WO | WO96/16624 | 6/1996 |
| WO | WO96/19173 | 6/1996 |
| WO | WO97/11659 | 4/1997 |
| WO | WO97/17922 | 5/1997 |
| WO | WO98/16179 | 4/1998 |
| WO | WO98/16180 | 4/1998 |
| WO | WO98/43684 | 10/1998 |
| WO | 10-328232 | 12/1998 |
| WO | WO99/13813 | 3/1999 |
| WO | WO99/34841 | 7/1999 |
| WO | WO99/51178 | 10/1999 |
| WO | WO00/00235 | 1/2000 |
| WO | WO00/32145 | 6/2000 |
| WO | WO00/59430 | 10/2000 |
| WO | WO01/15647 | 3/2001 |
| WO | WO01/26596 | 4/2001 |

(56) References Cited

FOREIGN PATENT DOCUMENTS

| | | |
|---|---|---|
| WO | WO02/07663 | 1/2002 |
| WO | WO02/32962 | 4/2002 |
| WO | WO02/064877 | 8/2002 |
| WO | WO02/067809 | 9/2002 |
| WO | WO03/009794 | 2/2003 |
| WO | WO03/053297 | 7/2003 |
| WO | WO03/105738 | 12/2003 |
| WO | WO2004/021946 | 3/2004 |
| WO | WO2004/049995 | 6/2004 |
| WO | WO2004/071539 | 8/2004 |
| WO | WO2004/084784 | 10/2004 |
| WO | WO2004/105664 | 12/2004 |
| WO | WO2005/018694 | 3/2005 |
| WO | WO2005/087164 | 9/2005 |
| WO | WO2006/104024 | 5/2006 |
| WO | WO2006/059922 | 6/2006 |
| WO | WO2006/062258 | 6/2006 |
| WO | WO2006/066029 | 6/2006 |
| WO | WO2006/083584 | 8/2006 |
| WO | WO2006/134904 | 12/2006 |
| WO | WO2006/134906 | 12/2006 |
| WO | WO2007/000315 | 1/2007 |
| WO | WO2007/046052 | 4/2007 |
| WO | WO2007/047598 | 4/2007 |
| WO | WO2007/049725 | 5/2007 |
| WO | WO2007/061035 | 5/2007 |
| WO | WO2007/142145 | 12/2007 |
| WO | WO2007/148502 | 12/2007 |
| WO | WO2008/018922 | 2/2008 |
| WO | WO2008/065945 | 6/2008 |
| WO | WO2008/146749 | 12/2008 |
| WO | WO2008/155699 | 12/2008 |
| WO | WO2009/004941 | 1/2009 |
| WO | WO2009/005431 | 1/2009 |
| WO | WO2009/139248 | 1/2009 |
| WO | WO2009/139255 | 1/2009 |
| WO | WO2009/041223 | 4/2009 |
| WO | WO2009/096108 | 8/2009 |
| WO | WO2009/107435 | 9/2009 |
| WO | WO2009/122830 | 10/2009 |
| WO | WO 2009/152018 A1 | 12/2009 |
| WO | WO2009/155264 | 12/2009 |
| WO | WO2009/155265 | 12/2009 |
| WO | WO2010/071508 | 6/2010 |
| WO | WO2010/074319 | 7/2010 |
| WO | WO2010/107096 | 9/2010 |
| WO | WO2010/114052 | 10/2010 |
| WO | WO2010/117015 | 10/2010 |
| WO | WO2011/053044 | 5/2011 |
| WO | WO2011/118725 | 9/2011 |
| WO | WO2011/118842 | 9/2011 |
| WO | WO2011/145653 | 11/2011 |
| WO | WO2011/150955 | 12/2011 |
| WO | WO2011/163582 | 12/2011 |
| WO | WO2012/002252 | 1/2012 |
| WO | WO2012/014436 | 2/2012 |
| WO | WO2012/042908 | 4/2012 |
| WO | WO2012/043077 | 4/2012 |
| WO | WO2012/043078 | 4/2012 |
| WO | WO2012/052172 | 4/2012 |
| WO | WO2012/043082 | 5/2012 |
| WO | WO2012/067216 | 5/2012 |
| WO | WO2012/073449 | 6/2012 |
| WO | WO2012/073499 | 6/2012 |
| WO | WO2012/090508 | 7/2012 |
| WO | WO2012/091016 | 7/2012 |
| WO | WO2012/101934 | 8/2012 |
| WO | WO2012/102034 | 8/2012 |
| WO | WO2012/117824 | 9/2012 |
| WO | WO2012/132460 | 10/2012 |
| WO | WO2012/170778 | 12/2012 |
| WO | WO2012/170779 | 12/2012 |
| WO | WO2012/170781 | 12/2012 |
| WO | WO2012/170808 | 12/2012 |
| WO | WO2012/174026 | 12/2012 |
| WO | WO2013/001788 | 1/2013 |
| WO | WO2013/060733 | 5/2013 |
| WO | WO2014/078247 | 5/2014 |

\* cited by examiner ional Patent Convention Application 11169395.8, filed Jun. 10, 2011, the substance of which is incorporated herein by reference.

METHOD AND APPARATUS FOR MAKING ABSORBENT STRUCTURES WITH ABSORBENT MATERIAL

CROSS REFERENCE TO RELATED APPLICATION

This application claims priority to European Patent Convention Application 11169395.8, filed Jun. 10, 2011, the substance of which is incorporated herein by reference.

FIELD OF THE INVENTION

The present disclosure relates to a method for making specific absorbent structures with absorbent material, optionally with longitudinally extending strips that are free of absorbent material, and apparatus for making such absorbent structures, and specific absorbent structures obtained therewith, suitable for absorbent articles, such as diapers and sanitary napkins.

BACKGROUND OF THE INVENTION

Absorbent articles, such as diapers and sanitary napkins, absorb and contain body exudates. They also are intended to prevent body exudates from soiling, wetting, or otherwise contaminating clothing or other articles, such as bedding, that come in contact with the wearer. A disposable absorbent article, such as a disposable diaper, may be worn for several hours in a dry state or in a urine-loaded state. Accordingly, efforts have been made toward improving the fit and comfort of the absorbent article to the wearer, both when the article is dry and when the article is fully or partially loaded with liquid exudate, while maintaining or enhancing the absorbing and containing functions of the article.

Efforts have also been made to make absorbent article thinner when dry, to improve the comfort of such articles.

Some absorbent articles, like diapers, contain absorbent material such as super absorbent polymers that absorbs very high quantities of liquid and causes the absorbent article to swell significantly. Such articles will thus increase significantly in volume during use, and sometimes in particular in the crotch area between the wearer's legs, which may render the article uncomfortable.

There may thus still be a need to further improve the performance/fit of such articles and/or the liquid transportation away from the crotch. There may also still be a need to further reduce the chance of leakage and to improve the efficiency of absorbency of an absorbent article, such as a diaper.

It has been found that improved liquid transportation can be achieved by the provision of transportation channels for distributing liquid in the absorbent article, e.g., the absorbent structure thereof. Furthermore, it has been found that improved fit can be obtained by providing absorbent articles with absorbent structures wherein the absorbent material is structured in longitudinal direction, optionally with areas that comprise less or no absorbent material, for improved bending flexibility in use (in the direction corresponding to the longitudinal direction (e.g., this may be the machine direction). The present disclosure provides an apparatus and method for providing such absorbent structures, and specific absorbent structures obtained thereby.

SUMMARY OF THE INVENTION

The present disclosure provides a method of making an absorbent structure having an absorbent layer and therein longitudinally extending strips that are substantially free of absorbent material (100), said absorbent layer being supported on a supporting sheet (200), said method comprising the steps of:

i) providing a feeder (20; 60) with absorbent material (100);
ii) providing a moving endless surface (30), such as for example a drum, moving in a machine direction (MD) having an outer shell with one or more forming receptacles (33), having an average longitudinal dimension and length (which may be in MD) and having an average transverse dimension and width (which may be in CD), said length being more than said width, said receptacle(s) comprising a multitude of substantially longitudinally extending rods (36), spaced apart from one another in transverse direction, each rod (36) having a maximum transverse dimension which is at least 0.3 mm and each of said rods (36) having a top portion and an opposing bottom portion, said bottom portion optionally being adjacent an inner grid (37), and the minimum distance in transverse dimension between neighboring rods (36) being at least 1 mm, and said rods (36) each having an average height dimension (perpendicular to the transverse and longitudinal dimensions) of at least 1 mm,
said moving endless surface (30) being connected to one or more vacuum systems (38) applying a vacuum suction to said receptacles (33) or part thereof,
iii) providing a supporting sheet (200) transporter (210);
iv) transporting said supporting sheet (200) to said outer shell, onto said top portions of said rods (36);
v) optionally pulling said supporting sheet (200) partially in between neighboring rods (36) by said vacuum suction, to form undulations (201) in said supporting sheet (200) between said rods (36) and to form crests (202) on said upper portion of said rods (36) (as for example shown in FIG. 4);
vi) depositing with said feeder said absorbent material (100) onto said supporting sheet (200) present on said forming receptacles (33);
vii) pulling said absorbent material (100) with said vacuum suction onto the supporting sheet (200) that is present between neighboring rods (36), to form absorbent strips, optionally into said undulations (201);
viii) optionally removing absorbent material (100) remaining on said crests (202) of said supporting sheet (200);
ix) removing said supporting sheet (200) and said absorbent material (100) from said moving endless surface (30);
to obtain said absorbent structure.

The present disclosure also provides an apparatus (1) for making an absorbent structure having an absorbent layer and therein substantially longitudinally extending strips that are substantially free of absorbent material (100), said layer being supported on a supporting sheet (200), said apparatus (1) comprising:
a feeder for feeding an absorbent material (100) to a moving endless surface (30),
a supporting sheet (200) transporter (210), for transporting a supporting sheet (200) to said moving endless surface (30); and
said moving endless surface (30) moving in a machine direction (MD) having an outer shell with one or more forming receptacles (33), as mentioned above, having a multitude of substantially longitudinally extending rods (36), each rod (36) having a maximum transverse dimension of at least 0.3 mm, each of said rods (36) having a top portion (surface) and an opposing bottom portion (surface), said bottom portion being adjacent an inner grid (37), and the minimum distance in transverse dimension between neighboring rods (36) being at least 1 mm, and said rods (36) having an average height dimension (perpendicular to the transverse and longitudinal dimensions) of at least 1 mm; and said moving endless surface (30) comprising a vacuum system (38) applying a vacuum suction to said receptacles (33) or part thereof; or any of the dimensions as describe above; and said feeder optionally being a further moving endless surface (20) with reservoir(s) for receiving and retaining a said absorbent material (100) and transferring said absorbent material (100) to said moving endless surface (30), said further moving endless surface (20) being connected to a vacuum system (28) to apply vacuum suction to said reservoir(s).

In some embodiments, in step vii), said absorbent structure comprise an absorbent layer with absorbent material (100) formed into substantially longitudinally extending strips of absorbent material (100) on said supporting sheet (200), optionally in said undulations (201), with therein between strips with substantially no absorbent material (100), optionally on said crests (202).

In some embodiments, step viii) is performed; hereto the supporting sheet (200) placed on the receptacle, or the part thereof that is to overlap with the receptacle, may be wider than the width of the receptacle, so-called over-in-feeding of the supporting sheet (200) in transverse dimension, e.g. in the transverse direction, for example the Cross-machine dimension (CD). The receptacle(s) may have a first average width (e.g. in CD) dimension and said supporting sheet (200) on said receptacle (33) has a second average width dimension (e.g. in CD), and the ratio of said first to said second average width dimension is at least 1:1.1, or at least 1:1.2, or at least 1:1.3, typically up 1:3.

The method may comprise the step of providing a first adhesive application unit (50), and applying an adhesive to said absorbent layer prior to removing it from said moving endless surface (30), or immediately subsequent thereto, and/or the step of providing a second adhesive application unit (51), and applying an adhesive to said supporting sheet (200), prior to deposition of said absorbent material (100) thereon; for example, this may be done selectively, either to the areas of the supporting sheet (200) that are to meet with the rods (36), or the areas of the supporting sheet (200) that are to be in between neighboring rods (36); for example said adhesive may be applied only in substantially longitudinal stripes on the areas of said supporting sheet (200) that coincides with said crests (202).

The method may be to provide a laminate of two of said absorbent structures, e.g. the method may be such that said steps i) to vii) and ix), and optionally step vii) are repeated to form a second absorbent structure, and wherein the method comprises the subsequent step of combining said first absorbent structure and said second absorbent structure, such that said absorbent materials (100) of both structures are sandwiched between said supporting sheet (200) of the first structure and the supporting sheet (200) of the second structure.

Some or each of said rods (36) may for example have said maximum transverse dimension which is at least 1 mm, or at least 2 mm, or for example at least 3 mm or at least 4 mm, and typically up to 20 mm or up to 15 mm or up to 10 mm; the minimum distance transversely in between neighboring rods (36) may for example be at least 2 mm, or at least 3 mm, or at least 5 mm, or at least 10 mm, and for example up to 30 mm, or up to 20 mm; said rods (36) each may have an average height dimension of for example at least at least 2 mm, or for example at least 3 mm. There may for example be at least 5 rods (36), or for example at least 7 rods (36).

The method may comprise the step of providing a pressure roll (70) with a raised pressure pattern (71), corresponding to the pattern of said rods (36) and/or said crests (202) if present, and mating said pressure roll (70) pattern with said absorbent structure, on the supporting sheet thereof, and/or on a further material, after such a further material is superposed on said absorbent layer, (e.g. the supporting sheet (200) is folded over it, a further supporting sheet (300) is placed on it, or and acquisition layer is placed on it, or a further absorbent structure is placed on it, such that the absorbent material (100) is sandwiched between the two supporting sheets (200; 300), wherein said pressure pattern (71) mates with said supporting sheet (200), or said further material, in the areas where, on the opposite surface, no absorbent material (100) is present Said feeder is adjacent and in close proximity to said moving endless surface (30), and they transfer of said absorbent material (100) takes place in a so-called meeting point. The feeder may be a further moving endless surface (20) with reservoir(s), such as a so-called print roll, and said method may comprise the steps of receiving absorbent material (100) on said further moving endless surface (20), retaining said absorbent material (100) in said reservoir(s) and transferring said absorbent material (100) to said moving endless surface (30); optionally said further moving endless surface's reservoir being formed by a multitude of grooves or a multitude of rows of cavities (22), each groove or row extending substantially longitudinally, said grooves or rows may be spaced from one another with raised strips. The method may comprise the step that said raised strips and said rods (36) are mating during the transfer of said absorbent material (100), e.g. in said meeting point.

Said receptacle (33) may have a front edge zone, and back edge zone, each extending the width/transverse dimension of said receptacle, and said front edge zone and/or back edge zone do not comprise said rods (36), with therein between a central zone with rods (36); or wherein said receptacle (33) has a centre region, front region and back region, and said receptacle (33) comprises said rods (36) in said front region only, or in said centre region only, or in said front and centre region only. Said receptacle (33) may have in said region(s) or zone(s) that not comprising said rods (36) a higher friction than said rods (36).

For example, as also shown in FIG. 6 for example, said central zone (B) having said rods, having a lower friction than said front edge zone and back edge zones (A; C) without rods. This can aid to ensure the supporting sheet (200) is pulled in between the rods (36) in the low friction zone, and less or not at all in the high friction zone.

The apparatus (1) may comprises additional units, such as a unit (300) to cover the absorbent structure's absorbent layer with a further material, as described herein; and/or an adhesive application unit (51) upstream from said moving endless surface (30), and/or a adhesive application unit (50), positioned downstream of the point where the feeder and said moving endless surface (30) meet (meeting point); and/or a pressure roll (70) with a raised pressure pattern (71), as described herein.

The present disclosure also relates to absorbent structures obtainable with the method or apparatus (1) herein, in particular those where the absorbent layer comprises such strips that comprise no absorbent material (100), and/or wherein said supporting sheet (200) comprises said undulations (201) with absorbent material (100) and crests, not comprising absorbent material (100), and/or wherein an adhesive is applied to immobilize said absorbent material (100), and/or wherein said absorbent structure comprises a further material on said absorbent layer, e.g. another absorbent structure, further supporting sheet (300) or acquisition layer, and a pressure is applied, to pressurize said supporting sheet (200) (further) into said strips where no absorbent material (100) is present, to render said strips more permanent in use.

The absorbent material (100), e.g. including or being a particulate superabsorbent polymer material, may be deposited on the supporting sheet (200) such that the absorbent layer comprises or consists of absorbent material (100) strips, extending substantially in the longitudinal direction, with therein between strips with no absorbent material (100), e.g. in the form of an absorbent layer with absorbent material (100) with therein substantially longitudinally extending strips that are free of absorbent material (100); such strips without absorbent material (100) may for example only extend at the most 90% or at the most 80%, or for example at the most 70% or for example at the most 60% of the full length of the absorbent layer. Said strips without absorbent are material may optionally have an average width dimension of at least 2 mm, or at least 3 mm; said strips may have any of the dimensions and shapes and positions described herein for said rods (36) and/or raised portions.

It should be understood that above and following description applies equally to the method and the apparatus (1) of the present disclosure, and the absorbent structure obtained therewith, unless stated otherwise.

DETAILED DESCRIPTION OF THE INVENTION

Figure 1:
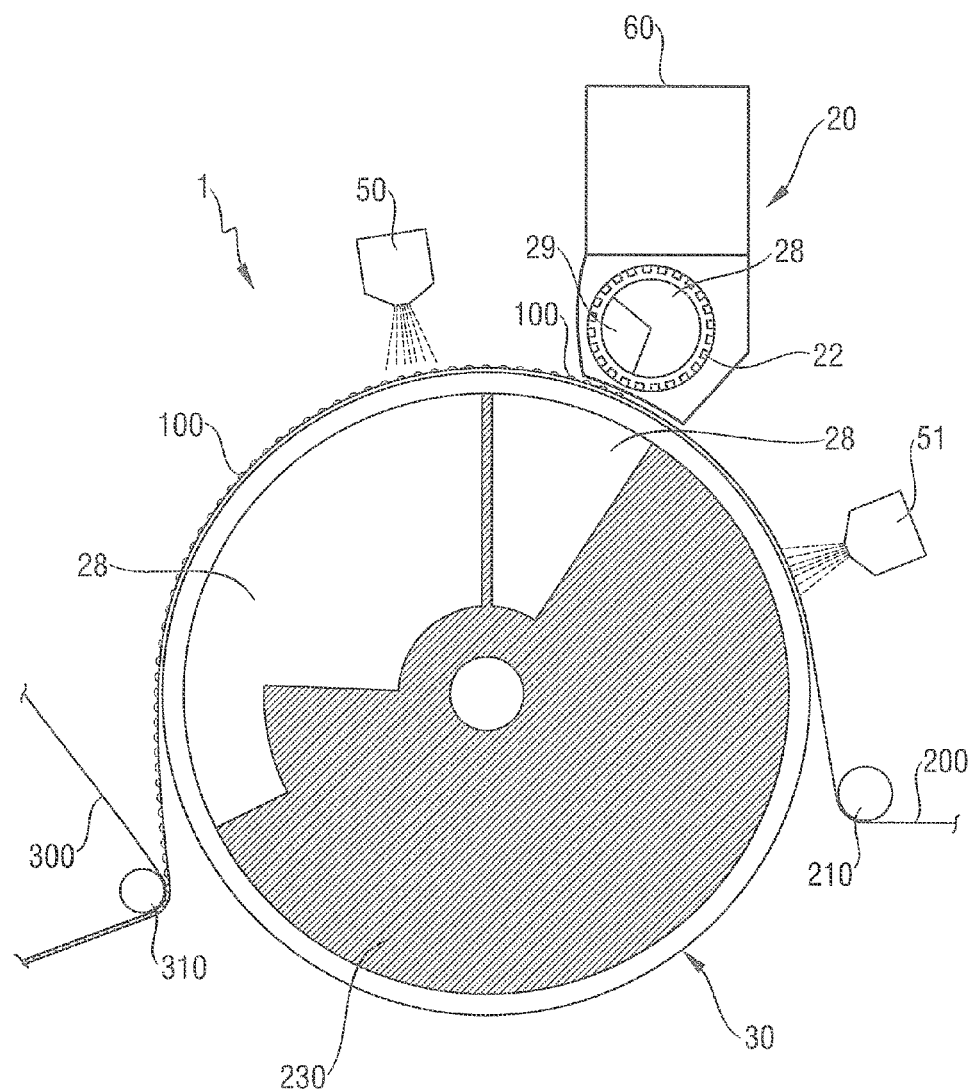
FIG. 1 is a schematic view of an apparatus of the present disclosure.

As summarized above, this invention encompasses a method and apparatus (1) for making an absorbent structure useful for absorbent article comprising absorbent material (100), optionally at least, or only, particulate superabsorbent polymer material, and preferred absorbent layers. Embodiments of such method and apparatus (1) and resulting absorbent structures and absorbent articles are further described herein below, after the following definitions.
Definitions "Absorbent structure" refers to a three-dimension structure with a longitudinally dimension and perpendicular thereto a transverse dimension and perpendicular to both a height dimension, and that comprises at least an absorbent material (100) and a supporting sheet (200), and that is useful in an absorbent article.

"Absorbent layer" refers to a three dimensional layer of absorbent material (100), formed by deposition of absorbent material (100) (s) onto the supporting sheet (200), and it may comprise other components, e.g. deposited onto the supporting sheet (200).

"Absorbent material (100)" refers to a material or mixture of materials that can absorb and retain bodily fluids; it typically includes or consists of Superabsorbent polymer material". "Superabsorbent polymer material" (also known as "absorbent gelling material," or "AGM," "superabsorbent,") refer to polymeric materials that can absorb at least 10 times their weight of an aqueous 0.9% saline solution as measured using the Centrifuge Retention Capacity test (Edana 441.2-02) i.e. having a CRC of at least 10 g/g. This is typically in particulate form.

"Particulate" is used herein to refer to a material which is in particulate form so as to be flowable in the dry state.

"Absorbent article" refers to a device that absorbs and contains body exudates, and, more specifically, refers to devices that are placed against or in proximity to the body of the wearer to absorb and contain the various exudates discharged from the body. Absorbent articles may include adult and infant diapers, including pants, such as infant training pants and adult incontinence undergarments, and feminine hygiene products, such as sanitary napkins and panty-liners and adult in continent pads, and breast pads, care mats, bibs, wound dressing products, and the like. Absorbent articles may further include floor cleaning articles, food industry articles, and the like. As used herein, the term "body fluids" or "body exudates" includes, but is not limited to, urine, blood, vaginal discharges, breast milk, sweat and fecal matter.

"Diaper" refers to an absorbent article generally worn by infants and incontinent persons about the lower torso so as to encircle the waist and legs of the wearer and that is specifically adapted to receive and contain urinary and fecal waste.

"Pant" or "training pant", as used herein, refer to diaper having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaperpants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

A "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Substantially cellulose free" is used herein to an absorbent layer structure (or core), that contains less than 5% by weight cellulosic fibers.

"Thickness" and "height" are used herein interchangeably.

A absorbent structure and absorbent layer thereof, and a receptacle (33) herein each have a longitudinal dimension and average length, and this may be corresponding the machine direction (MD), and perpendicular thereto a transverse dimension, and average width, which may be corresponding to the cross-machine direction (CD), said width being less than said length; and a front region, back region and central region, each being ⅓ of the average length of the structure/layer, respectively, and having each the full width. Each has longitudinal edges and edge zones, extending the full length thereof—as further described below.

Moving Endless Surface (30)

The method and apparatus (1) herein deploy a moving endless surface (30), moving in a machine direction (MD). It has an outer shell with one or more forming receptacles (33), for receiving thereon or therein the supporting sheet (200) (which may be a web material, as described herein below, or individual sheets that are placed on a receptacle). The following is described for a single receptacle (33) but may apply to each receptacles (33) of the moving endless surface (30)'s outer shell. An exemplary apparatus is shown in FIG. 1.

Each receptacle (33) corresponds typically to an absorbent structure to be produced, as suitable for an absorbent article. The supporting sheet (200) may be a web material, so the method and apparatus (1) herein can thus serve to produce a web of such absorbent structures that are then subsequently separated into individual structures.

The moving endless surface (30) may have or be a rotating surface, such as a rotating, e.g. cylindrical, drum. It may be that the outer shell moves, e.g. rotates, around a stationary inner chamber, e.g. a so-called stator (230).

The outer shell and the receptacle (33) have a transverse direction and average transverse dimension (average width), and the receptacle (33) has longitudinal direction and average longitudinal dimension (average length), perpendicular thereto.

The receptacle (33) has peripheral edges, and peripheral edge zones, including opposing longitudinal edges and edge zones, and a transverse front edge and front edge zone A, and a transverse back edge and back edge zone C, with a central zone B in between. Each of said front and back edge zones, extending the complete transverse dimension, may for example be in longitudinal dimension from about 5% to about 20%, or to 15%, or to 10% of the average longitudinal dimension of the receptacle.

Each of said longitudinal edge zone may extend the length and may have an average transverse dimension of for example from about 5% to about 20%, or typically to about 15% or to about 10% of the average transverse dimension of the receptacle.

The receptacle (33) may in addition, or alternatively, comprise a front region, back region and central region, therein between, as further described below. The central region may be for example the central ⅓ of the receptacle, extending the full transverse dimension.

Figure 2:
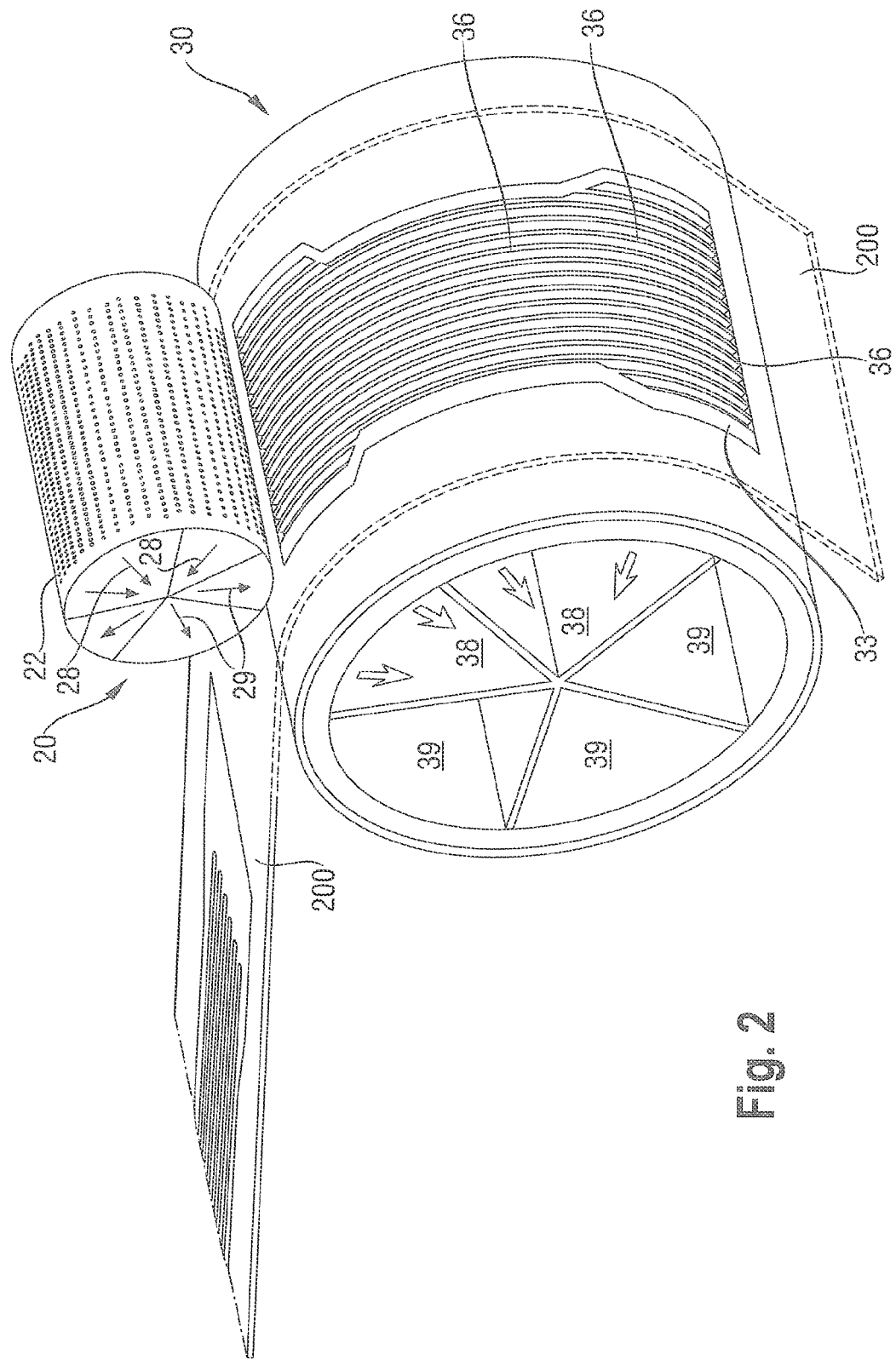
FIG. 2 is a perspective view of an apparatus of the present disclosure.
Figure 4:
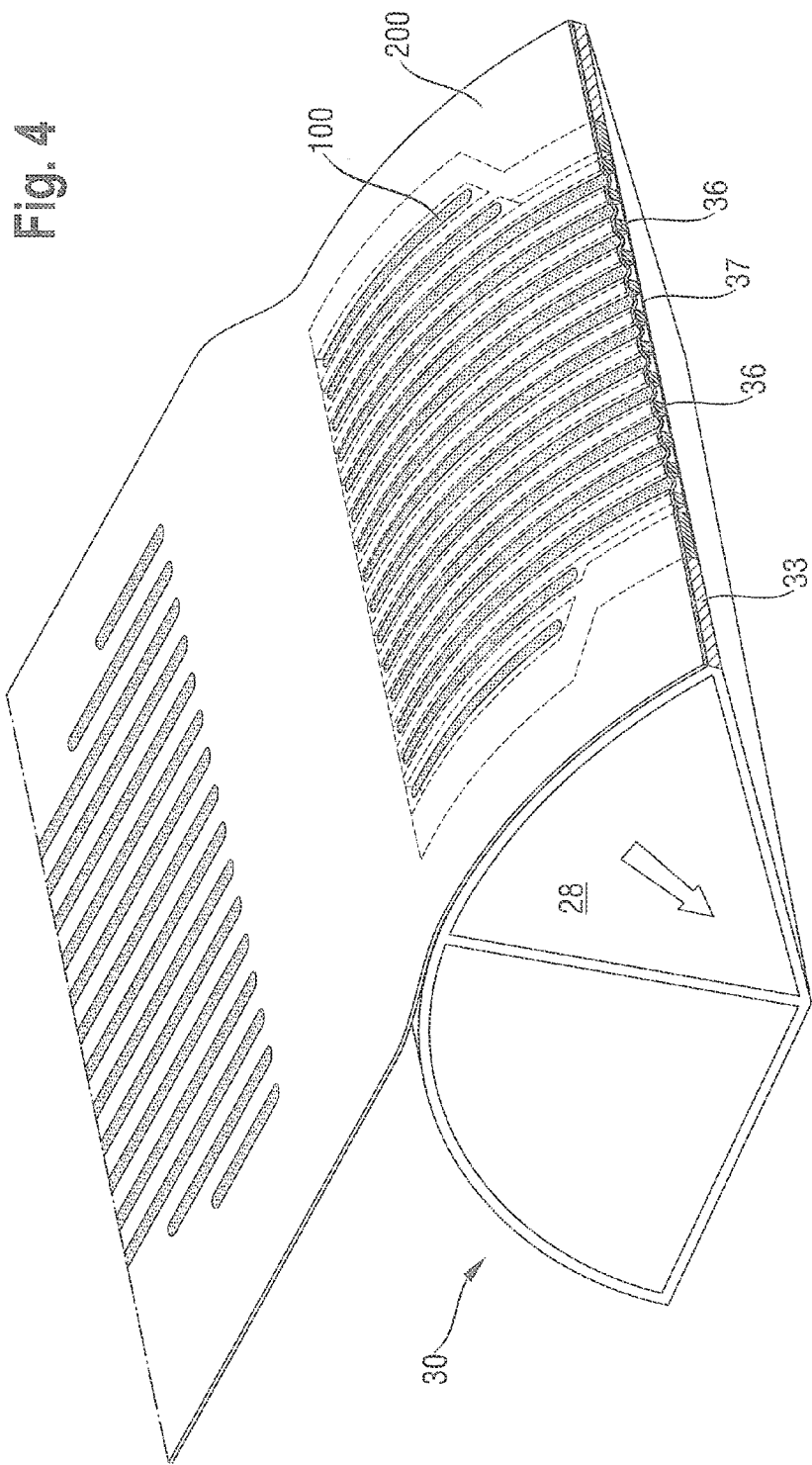
FIG. 4 is a partial and cross-sectional view of a moving endless surface and a receptacle thereof, of an apparatus of the present disclosure.

The receptacle (33) comprises a multitude of substantially longitudinally extending rods (36), spaced apart from one another in transverse direction. The rods (36) are such that they form or partially form the most outer surface of said receptacle, so that the supporting sheet (200) is received and carried by said rods (36). Thus, between rods (36) there is a spacing where the supporting sheet (200) may not be supported directly by the receptacle, or may not be in direct contact with the receptacle. For example, FIG. 2 shows such a receptacle, and FIG. 4 shows a cross-section thereof.

The receptacle (33) may comprise said rods (36) over substantially the whole length of the receptacle; or for example over the whole length except the front edge zone and/or back edge zone; or, in some embodiments herein, the rods (36) may be present only in said central region; in some embodiments, the rods (36) may be present in the front region and optionally the central region, but not the back region; in some embodiments, the rods (36) may be present in the back region and optionally the central region, but not the front region.

The receptacle (33) may comprise such rods (36) over the whole width of said receptacle; or for example over the whole width except in said longitudinal edge zones.

In any of these embodiments, the zone(s) or region(s) not comprising said rods (36) is herein referred to as rod-free zone or rod-free region; in said rod-free region or rod-free zone the supporting sheet (200) may be deposited onto said inner grid (37) (e.g. a mesh material) directly, or there may be an outer grid present, typically in the same plane as the rods (36); for example an outer grid made of a combination of transverse and longitudinal rods (36) that are intersecting in the same plane, like a mesh), or a plate with optionally apertures for vacuum suction. This is for example shown in FIG. 4.

Said receptacle (33) may have in said region(s) or zone(s) that not comprising said rods (36) a higher friction than aid rods (36). This can aid to ensure the supporting sheet (200) is pulled in between the rods (36) in the low friction zone, and less or not at all in the high friction zone. For example, the receptacle (33) can be made of a higher friction material (e.g. a material with a less even surface), or may be treated with an friction-increasing agents, in those zones or regions not comprising said rods (36); or for example said zones or regions with rods (36), or only said rods (36), can be made of a lower friction material, or treated with friction-reducing agent.

A rod (36) is considered substantial longitudinally extending, if its longitudinal (length) extension is more than its transverse (width) extension. Thus, a rod (36) may be under an angle with the longitudinal axis of the receptacle, provided said angle is less at the most 30°; or a rod (36) may be slightly curved (as described below); or a rod (36) may be wavy; or a rod (36) may comprise an angle, provided said angle is at least 120°, as described below; provided, in each case, its longitudinal (length) extension is more than its transverse (width) extension, e.g. they extend at least 50% or at least 100% more in longitudinal dimension of said receptacle (33) than in transverse dimension.

The rod (36) may be any shape or form. It may have a square, rectangular, round, oval or hexagonal cross-section in transverse dimension, for example. Each rod (36) has a top portion (which may be the top surface for, for example, rods (36) that have a square or rectangular cross-section) and an opposing bottom portion or surface. Said top portion or surface is then in contact with the supporting sheet (200); said bottom surface may be adjacent (e.g.: on) an, at least partially, air-permeable inner grid (37).

In some embodiments, it may be preferred that the rod (36) is generally rectangular with optionally a triangular-shaped top portion.

Neighboring rods (36) are spaced apart, e.g. with a minimum distance (transversely) of for example at least 2 mm, or at least 3 mm, or at least 5 mm, or for example at least 10 mm.

Two or more rods (36) may be parallel to one another, so that the spacing distance between parallel neighboring rods (36), transversely, is at least said 2 mm along substantially the whole length.

Thus, there is a void volume neighboring rods (36), e.g. between the inner grid (37) if present, and neighboring rods (36), and said void volume extends substantially in longitudinal direction in between said neighboring rods (36).

This void volume can serve to receive the supporting sheet (200) therein, as an undulation, and optionally said absorbent material (100).

Each rod (36) has a maximum transverse dimension which may be at least 0.3 mm, optionally at least 0.5 mm, or at least 1.0 mm, or at least 2 mm, and in some embodiments, for example at least 3 mm or at least 4 mm, and for example up to 20 mm, or up to 15 mm or for example up to 10 mm.

Each rod (36) has a maximum and average height dimension. Each rod (36) may for example have an average or maximum height dimension of at least 2 mm, or at least 3 mm, or at least 4 mm, or at least 5 mm.

This may be optionally substantially equal to the distance from the top of a rod (36) to the inner grid (37), if present.

The receptacle (33) may for example have at least 2 such rods (36), or for example at least 4 such rods (36), or for example at least 5 or at least 7 such rods (36).

The rods (36) may be slightly curved (for example having a single curvature), having a curvature with a radius that is at least equal to, optionally at least 1.5 times or at least 2 times, the average transverse dimension of the receptacle; and/or having a curvature following for example the contour of the closest longitudinal side edge; and/or having multiple small curvatures, said rod(s) being then for example longitudinally extending wavy rod(s). In any such case, said rods (36) are considered to extend substantially longitudinally, as said out above.

In some embodiments the rods (36) are straight and parallel to the longitudinal axis of the receptacle.

In some embodiments it may be preferred that the rods (36) are concave, wherein the longitudinal centre of the rod (36) is closer to the longitudinal axis of the receptacle (33) than the end point(s), and wherein the radius of curvature is at least 1.5 times the transverse dimension of the receptacle, optionally at least 2 times.

The moving endless surface (30) is connected to a vacuum system (38) that can apply a vacuum on said outer shell/receptacles (33), to pull the supporting sheet (200) onto said outer shell/receptacles (33), and to retain the absorbent material (100) thereon. The moving endless surface (30) may thus move adjacent a vacuum system, such as a vacuum chamber (s) (38), that is present adjacent the outer shell (on the opposite side to the rods (36)). The vacuum chamber(s) may be present in a stator (230) around which the moving endless surface (30) rotates.

The outer shell is hence at least partially air-permeable, which means it is such that it in air communication with said vacuum system, e.g. provided affective vacuum pressure can be applied through said shell onto said supporting sheet (200). For example, the rods (36) themselves may for example not be air-permeable, i.e. not being in direct air communication with said vacuum system. The surface area between rods (36) should however generally be air-permeable. Hence, the inner grid (37) may be air-permeable, e.g. it may be a mesh material, for example.

Figure 5:
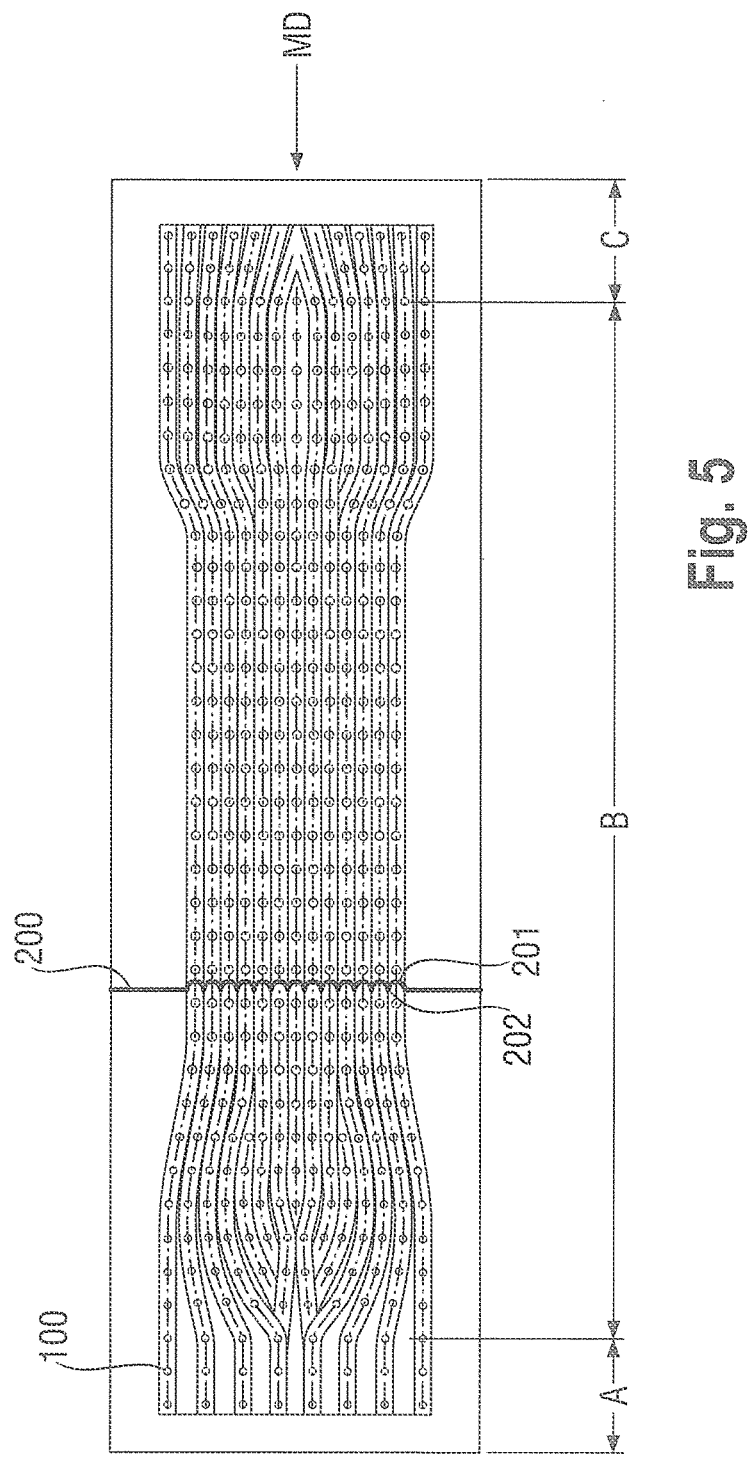
FIG. 5 is a top view of a receptacle during production of an absorbent structure herein.

In some preferred embodiments, the supporting sheet (200) is deposited onto said rods (36) and it bends in between neighboring rods (36), e.g. due to the vacuum suction to form thereby in said sheet undulations (201) between neighboring rods (36), and crests (202) supported on said rods (36) (on said top surface or top portion). The inner grid (37) may control/determine the size (height) of said undulations (201). This is for example shown in FIGS. 4 and 5.

The supporting sheet (200) is transferred from a transfer means, such a transfer roll, to said moving endless surface (30) and deposited onto said outer surface/receptacles (33), e.g. onto said rods (36) at least. It may be transported to the outershell and receptacles (33) thereof as a web, or as individual sheets.

The supporting sheet (200) may be a nonwoven material, as further described herein. Subsequently, said absorbent material (100) may be deposited onto said supporting sheet (200), on said receptacles (33). The absorbent material (100) may be deposited such that it is only present on the portions (e.g. strips) of the supporting sheet (200) that is present between neighboring rods (36), e.g. in said undulations (201). Thereto, specific feeders as described below may be used. Alternatively, or in addition, the vacuum may be such that it pulls the absorbent material (100) to or towards the portions of the supporting sheet (200) present between neighboring rods (36), e.g. into said undulations (201). Substantially no absorbent material (100) may for example be present on the supporting sheet (200) present on said rods (36), e.g. on said crests, as for example shown in FIGS. 4 and 5.

Alternatively, or in addition, absorbent material (100) deposited onto the portions of the supporting sheet (200) on said rods (36) (e.g. said crests (201)) may be removed by means known in the art, such as a scraper or doctor blade.

Alternatively, or in addition, the supporting sheet (200) may comprise adhesive. For example said adhesive may be present on said portions of said supporting sheet (200) that are between neighboring rods (36), e.g. said undulations (201). This may help to adhere the absorbent material (100) in such portions, e.g. on said undulations (201). The supporting sheet (200) may then, prior to addition of the absorbent material (100), comprise no adhesive applied on said portions supported by said rods (36), e.g. said crests (202), so that less or no absorbent material (100) adheres in said portions, e.g. crests. This is for example shown in FIG. 1.

By use of these rods (36), the absorbent structure may have said absorbent material (100) deposited in the form of strips of absorbent material (100) (e.g. corresponding to said undulations (201)), with therein in between strips that are free of such absorbent material (100) (e.g. corresponding to aid crests (202)); and/or said absorbent layer formed herein may be a layer of absorbent material (100) with strips that are substantially free of absorbent material (100) (e.g. the crests (202) of said supporting sheet (200)).

As described above, the supporting sheet (200) may be transferred to said moving endless surface (30) such that it forms undulations (201) and crests (202). Then, when the supporting sheet (200) is removed from said moving endless surface (30), the supporting sheet (200) is pulled substantially flat, resulting in an absorbent structure with substantially longitudinally extending strips (that correspond to the crests (202) of said material) that comprise substantially no absorbent material (100). This is for example shown in FIG. 5.

In some embodiments, the moving endless surface (30) may for example have a speed of at least 1000 part per minute and/or a speed of at least 4.5 m/s, or at least 6 m/s, or at least 8 m/s.

Feeder (20; 60)/Further Moving Endless Surface (20)

The absorbent material (100) may be delivered to the supporting sheet (200) by a feeder (60; 20) placed adjacent and in close proximity to said moving endless surface (30), for example substantially above said surface.

The absorbent material (100) may be deposited onto said supporting sheet (200) by any method, including substantially continuously.

The feeder herein is capable of holding the absorbent material (100), and letting it flow to the supporting sheet (200) on said moving endless surface (30). The point or area where the material leaves the feeder is herein referred to as meeting point.

The feeder may be a (e.g. stationary) hopper (60) with a container portion, to hold the material, e.g. having a volume of at least 1000 cm$^3$, and a guiding portion, e.g. a pipe-shapes portion, having one or more walls that guides the material from the container portion to the supporting sheet (200) on the moving endless surface (30).

In a preferred embodiment, the absorbent material (100) is deposited on the supporting sheet (200) carried on said moving endless surface (30) by a further moving endless surface (20) that moves, moving in a machine direction, e.g. rotates, adjacent and in close proximity to said moving endless surface (30). In such a case, a hopper (60), as for example described above, may feed the absorbent material (100) to this further moving endless surface (20).

The further moving endless surface (20) may be a rotating device. The further moving endless surface (20) is typically a rotating device with a certain radius, such as a cylinder or drum or print roll, as for example shown in the Figures. The radius of the further moving endless surface (20) may depend on what absorbent structure is produced, e.g. what size, and for example how many structures are produced per cycle of the further moving endless surface (20), e.g. print roll or drum. For example, the drum/print roll may have a radius of at least 40 mm, or of at least 50 mm; it may be for example up to 300 mm, or up to 200 mm.

The further moving endless surface (20) may have any suitable width, but for example a width corresponding to the width of the absorbent structure to be produced; this for example be at least 40 mm, or at least 60 mm, or for example up to 400 mm, or up to 200 mm.

Said further moving endless surface (20) may have one or more reservoirs with a certain volume for receiving said absorbent material (100) therein, and transporting it and then depositing it to said supporting sheet (200) on the moving endless surface (30) with receptacle(s) with rods (36), described above.

Such a reservoir may then correspond to an absorbent structure to be produced. The reservoir may have a (average) longitudinal dimension, and (average) length, and a (average) transverse dimension and (average) width, said length being more than said width.

The reservoir may have raised strips (that have no void volume) and then, when the further moving endless surface (20) moves (rotates) adjacent said moving endless surface (30) with said supporting sheet (200) on said rods (36), said raised portions may mate with (correspond to) said rods (36) (herein referred to as "mating"). Then, the absorbent material (100) is deposited selectively between rods (36), e.g. in said undulations (201).

In some embodiments, the reservoir is composed of multitude of groves, extending substantially longitudinally, or a multitude of rows of cavities (22), extending, for receiving the absorbent material (100) therein, wherein neighboring grooves or rows are being separated from one another by such raised strips that do not have a void volume for receiving absorbent material (100).

Then, typically, the raised strips move adjacent (mate) said rods (36) and said crests (202) of said supporting sheet (200), and the grooves or rows of cavities (22) move adjacent (mate) with said areas of the supporting sheet (200) between neighboring rods (36), e.g. said undulations (201). Then, the absorbent material (100) is deposited selectively between rods (36), e.g. in said undulations (201).

The resulting absorbent structure then comprises a supporting sheet (200) with thereon a layer of absorbent material (100) with substantially longitudinally extending strips that comprise no absorbent material (100).

The cavities (22) may have any dimensions and shape, including cubical, rectangular, cylindrical, semi-spherical, conical, or any other shape. This may be any suitable number of cavities (22), but for example at least 20 or at least 50.

The cavities (22) may be present as identical cavities (22) or they may vary in dimension(s) or shape. The exact pattern, dimensions etc. will depend on the required structure to be formed, but may for example also depend on the particle size of the absorbent material (100), process speed etc. In some embodiments at least 30% of the surface area of the reservoir of the further moving endless surface (20) comprises said cavities (22), optionally at least 40%, and optionally up to 55% or up to 50%.

The distance (longitudinally) between the centre point of a cavity (said centre point being in the plane of the outer surface of the further moving endless surface (20)) and the centre point of a neighboring cavity (in a row of cavities (22)) may for example be at least 3 mm, or at least 4 mm, or at least 6 mm, or for example up to 40 mm or up to 30 mm or up to 20 mm. This may apply to all such distances between neighboring cavities (22) longitudinally, or this may be an average over all such distances.

The distance transversely between the centre point of a cavity or groove (said centre point being in the plane of the outer surface of the further moving endless surface (20)) and the centre point of a neighboring cavity or groove (in a transverse line of cavities (22)) may for example also be as above. In some embodiments, the shortest distance transversely between two neighboring cavities (22) of a line of cavities (22) or between neighboring groves is at least 3.0 mm, or at least 4.0 mm, so that this can mate with the rods (36) of the moving endless surface (30).

Said rows or grooves may extend substantially parallel to, and equally spaced from, one another and/or said lines may extend substantially parallel to, and equally spaced from, one another.

In some embodiments, the grooves and rows have such a shape or pattern, that the distance between neighboring groves or rows is substantially corresponding to a rod; and/or that the grooves or rows correspond substantially to the areas between neighboring rods (36). Then the grooves or rows can mate with the areas between rods (36).

In some embodiments, the length dimension of a cavity may be (on average over all cavities (22) and/or for each cavity; measured over the outer surface of the further moving endless surface (20)) at least 1 mm, or at least 2 mm, or at least 4 mm, and for example at the most 20 mm or at the most 15 mm. The width dimension may be within the same ranges as above, or it may even be the same as the length dimensions for one or more or each cavity.

In some embodiments, a raised portion is completely overlapping a corresponding rod.

In some embodiments, the average width dimension of each raised portions of the reservoir(s) that mates with a rod (36) is about at least 10% more than the average width dimension of said rod.

The reservoir, cavities (22) or grooves may have any suitable dept dimension, and it may depend for example on the height of the further moving endless surface (20) (e.g. radius), the thickness/caliper of the desired structure to be produced, the particle size of the material, etc. The maximum depth of a reservoir, cavities (22) or grooves and/or the average maximum depth (average over all maximum depths of all cavities (22) and/or grooves) may for example be at least 1 mm, or at least 1.5 mm, or for example 2 mm or more, and for example up to 20 mm, or up to 15 mm, or in some embodiment herein, up to 10 mm, or to 5 mm, or to 4 mm.

According to some embodiments herein, the cavities (22) may have a an average width dimension and length dimension of from 2 to 8 mm or from 3 mm to 7 mm; and the cavities (22) may have a maximum depth and/or average maximum depth of for example from 1.5 mm to 4 mm.

A scraper or doctor blade may be used to remove excess absorbent material (100). Excess material may be removed from the reservoir and recycled back to e.g. the hopper One possibility to hold the material in the reservoir (or its groves or cavities (22)) may be a vacuum (28) applied to the inner side of the further moving endless surface (20), e.g. print roll or drum, in combination with suction holes in (the bottom) of the reservoir, or groves cavities (22) thereof, to thus apply the vacuum suction onto the absorbent material (100). The vacuum is for example released just before or at the meeting point. The vacuum may be any vacuum pressure such as, just as for the moving endless surface (30) above, for example at least 10 kPa, or at least 20 kPa.

The vacuum may be provided by providing one or a plurality of vacuum chambers (28) in said further moving endless surface (20) (e.g. in its interior), wherein said vacuum can be applied, reduced, increased, and released (disconnected), depending on the position thereof in the process/apparatus (1).

Additional air pressure and air pressure chamber(s) (29) may be used/applied to said absorbent material (100) close to or at the meeting point, to ensure that the material flows to the supporting sheet (200) on said moving endless surface (30).

Absorbent Material (100)

The absorbent material (100) herein is optionally a flowable material (in the dry state), such as a particulate material; it may be any material in particulate form, which includes particles, flakes, fibers, spheres, agglomerated particles and other forms known in the art. The absorbent material (100) may be a mixture of cellulose material, or so-called airfelt, and superabsorbent polymer material.

Alternatively, or in addition, when two absorbent structures are combined as described herein, the first absorbent structure may comprise a first absorbent material (100), and the second structure may comprise a second, different absorbent material (100), for example having a different capacity (CRC).

In some embodiments herein, the absorbent material (100), e.g. the particulate absorbent material (100), comprises at least or consists of (particulate) superabsorbent polymer material, herein referred to as SAP, and also known as particulate absorbent gelling material, AGM. The particulate SAP herein may have a high sorption capacity, e.g. having a CRC of for example at least 20 g/g, or at 30 g/g. Upper limits may for example be up to 150 g/g, or up to 100 g/g.

The particulate SAP may have a good permeability for liquid, for example, having a SFC value of at least $10 \times 10^{-7}$ cm$^3$ s/g; or optionally at least $30 \times 10^{-7}$ cm$^3 \cdot$s/g, or at least $50 \times 10^{-7}$ cm$^3$s/g $10 \times 10^{-7}$ cm$^3$s/g, or possibly permeability SFC value of at least $100 \times 10^{-7}$ cm$^3$s/g, or at least a SFC of $120 \times 10^{-7}$ cm$^3$sec/g. This SFC is a measure of permeability and an indication of porosity is provided by the saline flow conductivity of the gel bed as described in U.S. Pat. No. 5,562,646, (Goldman et al.) issued Oct. 8, 1996 (wherein however a 0.9% NaCl solution is used instead of Jayco solution). Upper limits may for example be up to 350 or up to 250 ($\times 10^{-7}$ cm$^3 \cdot$s/g).

In some embodiments herein the polymers of said SAP are internally cross-linked and/or surface crosslinked polymers.

In some embodiments herein, the absorbent material (100) comprising or consisting of particles of polyacrylic acids/polyacrylate polymers, for example having a neutralization degree of from 60% to 90%, or about 75%, having for example sodium counter ions, as known in the art, e.g. surface crosslinked and/or internally crosslinked and/or post-crosslinked polyacrylic acid/polyacrylate polymers.

In some embodiments herein, the absorbent material (100) is in the form of particles with, a mass medium particle size up to 2 mm, or between 50 microns and 2 mm or to 1 mm, or optionally from 100 or 200 or 300 or 400 or 500 μm, or to 1000 or to 800 or to 700 μm; as can for example be measured by the method set out in for example EP-A-0691133. In some embodiments of the present disclosure, the material is in the form of particles whereof at least 80% by weight are particles of a size between 50 μm and 1200 μm and having a mass median particle size between any of the range combinations above. In addition, or in another embodiment of the present disclosure, said particles are essentially spherical. In yet another or additional embodiment of the present disclosure the absorbent material (100) has a relatively narrow range of particle sizes, e.g. with the majority (e.g. at least 80% or optionally at least 90% or even at least 95% by weight) of particles having a particle size between 50 μm and 1000 μm, optionally between 100 μm and 800 μm, and more optionally between 200 μm and 600 μm.

The absorbent material (100) herein may advantageously comprise less than 15% by weight of water, or less than 10%, or less than 8% or less than 5%. The water-content can be determined by the Edana test, number ERT 430.1-99 (February 1999) which involves drying the particulate material (100) at 105° Celsius for 3 hours and determining the moisture content by the weight loss of the particulate material (100) after drying.

The particulate SAP herein may be particles of SAP that are surface coated or surface treated (this not including surface-crosslinking, which may be an additional surface-treatment); such coatings and surface treatment steps are well known in the art, and include surface treatment with one or more inorganic powders, including silicates, phosphates, and coatings of polymeric material, including elastomeric polymeric materials, or film-forming polymeric materials.

Supporting Sheet (200)

The absorbent structure producible with the apparatus (1) and method of the present disclosure comprises a supporting sheet (200), to receive the absorbent material (100). This supporting sheet (200) may be any individual sheet or web sheet material, in particular paper, films, wovens or nonwovens, or laminate of any of these.

In some embodiments herein, the supporting sheet (200) is a nonwoven, e.g. a nonwoven web, such as a carded nonwoven, spunbond nonwoven or meltblown nonwoven, and including nonwoven laminates of any of these.

The fibers may be of natural or man-made origin and may be staple or continuous filaments or be formed in situ. Commercially available fibers have diameters ranging typically from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). The fibers may be bicomponent fibers, for example having a sheet-core arrangement, e.g. with different polymers forming the sheet and the core. Nonwoven fabrics can be formed by many processes such as meltblowing, spunbonding, solvent spinning, electrospinning, and carding. The basis weight of nonwoven fabrics is usually expressed in grams per square meter (gsm).

The nonwoven herein may be made of hydrophilic fibers; "Hydrophilic" describes fibers or surfaces of fibers, which are wettable by aqueous fluids (e.g. aqueous body fluids) deposited on these fibers. Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A fiber or surface of a fiber is said to be wetted by a fluid (i.e. hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be hydrophobic if the contact angle is greater than 90° and the fluid does not spread spontaneously across the surface of the fiber.

The supporting sheet (200) herein may be air-permeable. Films useful herein may therefore comprise micro pores. Nonwovens herein may for example be air permeable. The supporting sheet (200) may have for example an air-permeability of from 40 or from 50, to 300 or to 200 m$^3$/(m$^2$×min), as determined by EDANA method 140-1-99 (125 Pa, 38.3 cm$^2$). The supporting sheet (200) may alternatively have a lower air-permeability, e.g. being non-air-permeable, to for example be better detained on a moving surface comprising vacuum.

In preferred executions, the supporting sheet (200) is a nonwoven laminate material, a nonwoven laminate web, for example of the SMS or SMMS type.

In order to form easily said undulations (201), the supporting sheet (200) may have a basis weight that is less than 60 gsm, or for example than 50 gsm, for example from 5 gsm to 40 gsm, or to 30 gsm.

Adhesive Application Units and Method Steps.

The supporting sheet (200) may comprise and adhesive prior to transfer to said moving endless surface (30). Thus, the apparatus (1) herein may comprise an adhesive application unit (51) upstream from said moving endless surface (30), and for example downstream from said supporting material transfer means (210), e.g. roll. The method herein may thus comprise such an adhesive application step. This is for example shown in FIG. 1.

This adhesive may be applied uniformly and/or continuously.

It may be applied as substantially longitudinal stripes. For example, the adhesive may be applied in substantially longitudinally extending stripes such that areas of the supporting sheet (200) with the stripes of adhesive are between neighboring rods (36), and the areas of the supporting sheet (200) that do not comprise said adhesive correspond to said rods (36), or the opposite.

In some embodiments, the apparatus (1) may comprise a unit to apply an adhesive to said supporting sheet (200) in a pattern, for example the pattern of the rods (36), or the pattern of the areas between the rods (36). This may be done by spraying, or for example by selectively slot-coating; the apparatus (1) may thus comprise a slot-coater, for example with a coating pattern that corresponds to the rods (36), or the areas between the rods (36).

Any suitable adhesive can be used for this, for example so-called hotmelt adhesives used. For example. A sprayable hot melt adhesives, such as H.B. Fuller Co. (St. Paul, Minn.) Product No. HL-1620-B, can be used.

Alternatively, or in addition, it may be beneficial to apply a further immobilization adhesive to said absorbent structure produced by the apparatus (1) or method herein, e.g. to ensure the absorbent material (100) will stay substantially in the applied pattern. This immobilization adhesive may then for example be applied onto said absorbent layer just after application of said absorbent material (100) onto said supporting sheet (200).

The apparatus (1) herein may thus have a further immobilization adhesive application unit (50), e.g. downstream from said moving endless surface (30)' meeting point. The method may have a corresponding method step. This is for example shown in FIG. 1.

This adhesive may be applied uniformly and/or homogeneously. This may be a thermoplastic adhesive material.

In accordance with certain embodiments, the thermoplastic adhesive material may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic adhesive material may be a hot melt adhesive comprising at least one thermoplastic polymer in combination with other thermoplastic diluents such as tackifying resins, plasticizers and additives such as antioxidants. In certain embodiments, the thermoplastic polymer has typically a molecular weight (Mw) of more than 10,000 and a glass transition temperature (Tg) usually below room temperature or $-6°$ C.$>$Tg$<16°$ C. In certain embodiments, typical concentrations of the polymer in a hot melt are in the range of about 20 to about 40% by weight. In certain embodiments, thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins. In exemplary embodiments, the tackifying resin has typically a Mw below 5,000 and a Tg usually above room temperature, typical concentrations of the resin in a hot melt are in the range of about 30 to about 60%, and the plasticizer has a low Mw of typically less than 1,000 and a Tg below room temperature, with a typical concentration of about 0 to about 15%. In certain embodiments, the thermoplastic adhesive material is present in the form of fibers. In some embodiments, the fibers will have an average thickness of about 1 to about 50 micrometers or about 1 to about 35 micrometers and an average length of about 5 mm to about 50 mm or about 5 mm to about 30 mm.

Further Method Steps/Apparatus (1) Units

The apparatus (1) and method herein may comprise the further step/unit, of applying a further supporting sheet (300) onto said absorbent structure, to enclose said absorbent material (100), as know in the art. This is for example shown in FIG. 1.

The apparatus (1) and method herein may alternatively or in addition comprise the apparatus (1) unit/method step of folding the supporting sheet (200) over the absorbent material (100) to enclose it thereby.

It may comprise a sealing unit, sealing step to seal the two supporting sheet (200) or the folded supporting sheet (200) along the peripheral edges of the absorbent structure/layer. The absorbent structure may alternatively or in addition be combined with other layers, such as an acquisition layer, or topsheet and the apparatus (1) and method herein may comprise according steps/units.

The method or apparatus (1) herein may be to produce an absorbent core or structure that comprises two or more of the above described absorbent structures; for example two such layers, superposed on one another such that the absorbent material (100) of a first layer and the absorbent material (100) of the other second layer are adjacent one another and sandwiched between the supporting sheet (200) of the first layer and the supporting sheet (200) of the second layer. This is for example shown in FIG. 3.

The apparatus (1) herein may thus be a combination apparatus (1), comprising two or more, e.g. two, of the apparatuses (1) described herein, to produce two or more, e.g. two, absorbent structures, and then comprising a combining unit to combine the absorbent structures. The method may comprise according method step(s).

The strips where no absorbent material (100) of one layer is present may then be superposed on the strips where no absorbent material (100) is present of the other layer, to form joined strips; alternatively, they may be alternating, so that a strip where no absorbent material (100) of one layer is superposed onto the absorbent material (100) of the other layer.

In some embodiments, when the two layers are combined, the center (referring to the width) of a (or of each of) the absorbent material (100) strips of one layer overlays and contacts the center of a (or of the respective) strip where no absorbent material (100) is present of the other layer, and optionally vice versa. Hence, one or more, or each, absorbent material (100) strip of the one layer may be placed centrally on or in the strip without absorbent material (100) of the other layer and vice versa.

The absorbent structure produced with the method/apparatus (1) of the present disclosure herein may also be combined with an absorbent structure produced by a method/apparatus (1) other than of the present disclosure, said combination may be done as set out above.

Figure 3:
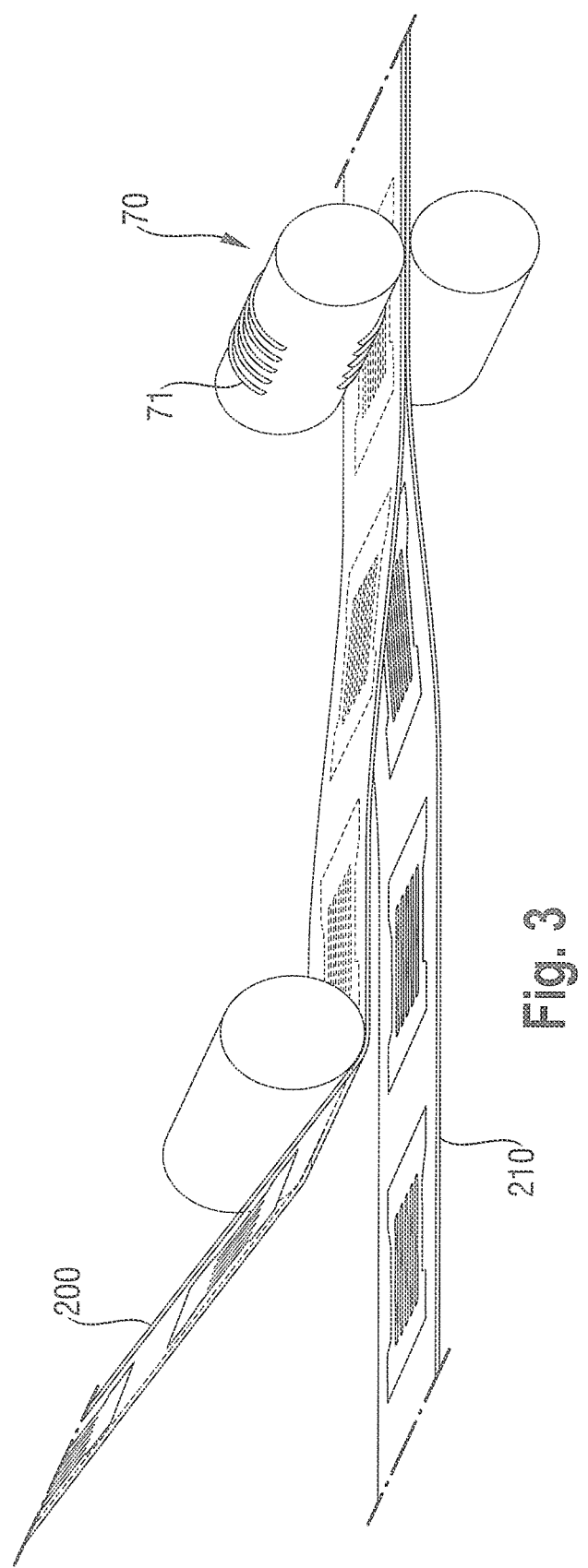
FIG. 3 is a perspective view of optional further units of the apparatus of the present disclosure, combining absorbent structures into an absorbent article and bonding it.

In some embodiments, the apparatus (1) may comprise a pressure means, such as a pressure roll (70), that can apply pressure onto the absorbent structure, and typically on the supporting sheet thereof, and/or onto the further material if combined with the absorbent structure as described herein; or as for example shown in FIG. 3, on one of the supporting sheets (200; 300) sandwiched on either side of the absorbent layer or layers.

The pressure may be applied selectively onto said supporting sheet (200) or on any of the further material/layer that placed over the absorbent layer, as described above in this section.

This pressure application may optionally be done to selectively apply pressure only onto the strips of the supporting sheet (s) (200; 300) or further material that comprise (on the opposed surface) no absorbent material (100), to avoid compaction of said absorbent material (100) itself.

Thus, the apparatus (1) may comprise a pressure means (70) that has a raised pressuring pattern (71) corresponding to said rods (36), so that the raised pressure pattern (71) can mate with the strips of the supporting sheet (200) that have no absorbent material (100) (on its surface), that are or were supported by said rods (36). The method may have an according method step.

Absorbent Articles

The apparatus (1) and method of the present disclosure are for example useful to produce absorbent structures, or absorbent cores (absorbent structures combined with a further material, as described herein) suitable for absorbent articles.

Absorbent articles may include diapers, including fastenable diapers and (refastenable) training pants; adult incontinence undergarments (pads, diapers) feminine hygiene products (sanitary napkins, panty-liners), breast pads, care mats, bibs, wound dressing products, and the like. As The absorbent article herein may comprise in addition to an absorbent structure or core produced by the method/apparatus (1) herein, a topsheet and backsheet, and for example one or more side flaps or cuffs. The topsheet or cuffs or side flaps may comprise a skin care composition or lotion or powder, known in the art, panels, including those described in U.S. Pat. Nos. 5,607,760; 5,609,587; 5,635, 191; 5,643,588.

Preferred absorbent articles herein comprise a topsheet, facing the wearer in use, for example a nonwoven sheet, and/or an apertured sheet, including apertured formed films, as known in the art, and a backsheet.

The backsheet may be liquid impervious, as known in the art. In preferred embodiments, the liquid impervious backsheet comprises a thin plastic film such as a thermoplastic film having a thickness of about 0.01 mm to about 0.05 mm. Suitable backsheet materials comprise typically breathable material, which permit vapors to escape from the diaper while still preventing exudates from passing through the backsheet. Suitable backsheet films include those manufactured by Tredegar Industries Inc. of Terre Haute, Ind. and sold under the trade names X15306, X10962 and X10964.

The backsheet, or any portion thereof, may be elastically extendable in one or more directions. The backsheet may be attached or joined to a topsheet, the absorbent structure/core herein, or any other element of the diaper by any attachment means known in the art.

Diapers herein may comprise leg cuffs and/or barrier cuffs; the article then typically has a pair of opposing side flaps and/or leg and/or barrier cuffs, each of a pair being positioned adjacent one longitudinal side of the absorbent structure/core, and extending longitudinally along said absorbent structure/core, and typically being mirror images of one another in the longitudinal axis (which may be MD axis) of the article; if leg cuffs and barrier cuffs are present, then each leg cuffs is typically positioned outwardly from a barrier cuff. The cuffs may be extending longitudinally along at least 70% of the length of the article. The cuff(s) may have a free longitudinal edge that can be positioned out of the X-Y plane (longitudinal/transverse directions) of the article, i.e. in z-direction. The side flaps or cuffs of a pair may be mirror images of one another in the longitudinal axis of the article. The cuffs may comprise elastic material.

The diapers herein may comprise a waistband, or for example a front waistband and back waist band, which may comprise elastic material.

The diaper may comprise side panels, or so-called ear panels. The diaper may comprise fastening means, to fasten the front and back, e.g. the front and back waistband. Preferred fastening systems comprise fastening tabs and landing zones, wherein the fastening tabs are attached or joined to the back region of the diaper and the landing zones are part of the front region of the diaper.

The absorbent article may also include a sub-layer disposed between the topsheet and the absorbent structure/core, capable of accepting, and distributing and/or immobilizing bodily exudates. Suitable sublayers include acquisition layers, surge layers and or fecal material storage layers, as known in the art. Suitable materials for use as the sub-layer may include large cell open foams, macro-porous compression resistant non woven highlofts, large size particulate forms of open and closed cell foams (macro and/or microporous), highloft non-wovens, polyolefin, polystyrene, polyurethane foams or particles, structures comprising a multiplicity of vertically oriented, optionally looped, strands of fibers, or optionally apertured formed films, as described above with respect to the genital coversheet. (As used herein, the term "microporous" refers to materials that are capable of transporting fluids by capillary action, but having a mean pore size of more than 50 microns. The term "macroporous" refers to materials having pores too large to effect capillary transport of fluid, generally having pores greater than about 0.5 mm (mean) in diameter and more specifically, having pores greater than about 1.0 mm (mean) in diameter, but typically less than 10 mm or even less than 6 mm (mean).

All patents and patent applications (including any patents which issue thereon) assigned to the Procter & Gamble Company referred to herein are hereby incorporated by reference to the extent that it is consistent herewith.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the present disclosure are, in relevant part, incorporated herein by reference; the citation of any document is not to be construed as an admission that it is prior art with respect to the present disclosure. To the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the present disclosure. It is therefore intended to cover in the appended claims all such changes and modifications that are within the scope of this invention.

What is claimed is:

1. A method of making an absorbent structure having an absorbent layer and therein longitudinally extending strips that are free of absorbent material, the absorbent layer being supported on a supporting sheet, the method comprising the steps of:

providing a moving endless surface moving in a machine direction (MD) having an outer shell with a forming receptacle, having an average width and transverse direction and dimension, and having an average length and longitudinal dimension, the average length being more than the average width; the receptacle comprising a multitude of substantially longitudinally extending rods, spaced apart from one another in a transverse direction, each rod having a maximum transverse width dimension of at least 0.3 mm and each of the rods having a top portion and an opposing bottom portion, the bottom portion being adjacent an inner grid, and the minimum distance transversely between neighboring rods being at least 1 mm, and the rods each having an average height dimension perpendicular to the transverse and longitudinal dimensions of at least 1 mm; the moving endless surface being connected to one or more vacuum systems applying a vacuum suction to the receptacle;

receiving absorbent material on a second moving endless surface comprising longitudinally extending rows of cavities, wherein the rows of cavities are separated from each other by raised strips;

retaining the absorbent material in the cavities;

applying adhesive to the supporting sheet in substantially longitudinal stripes;

transporting the supporting sheet to the outer shell, onto the top portions of the rods;

pulling the supporting sheet having the longitudinal stripes of adhesive partially in between neighboring rods by the vacuum suction, to form undulations in the supporting sheet between the rods and to form crests on the upper portion of the rods;

depositing absorbent material onto the supporting sheet present on the forming receptacle;

mating the raised strips and the rods during transfer of the absorbent material to the supporting sheet;

pulling the absorbent material with the vacuum suction into the undulations of the supporting sheet and onto the longitudinal stripes of adhesive between neighboring rods to form absorbent strips;
removing absorbent material remaining on the crests of the supporting sheet;
applying adhesive to the absorbent strips and the supporting sheet between the absorbent strips to form a first absorbent structure; and
removing the first absorbent structure from the moving endless surface;
repeating the previous steps to form a second absorbent structure; and
combining the first absorbent structure and the second absorbent structure with a pressure roll having a raised pressure pattern by applying pressure with the raised pressure pattern to the first absorbent structure and the second absorbent structure where no absorbent material is present, such that the absorbent layers of both structures are sandwiched between the supporting sheet of the first structure and the supporting sheet of the second structure.

2. The method of claim 1, wherein the receptacle has a front edge zone and a back edge zone, each zone extending the respective transverse dimension of the receptacle, and wherein the front edge zone and back edge zone do not comprise the rods.

3. The method of claim 1, wherein the receptacle has a first average width dimension and the supporting sheet, or portion thereof that is on the receptacle, has a second average width dimension, and the ratio of the first to the second average width dimension is at least 1:1.2.

4. The method of claim 1, wherein the supporting sheet is a nonwoven sheet and the absorbent material is a particulate superabsorbent polymer material.

5. The method of claim 1, wherein the rods have a maximum width dimension which is at least 2 mm and the minimum distance transversely between neighboring rods being at least 3 mm.

* * * * *